US012085573B2

(12) United States Patent
Hund et al.

(10) Patent No.: US 12,085,573 B2
(45) Date of Patent: Sep. 10, 2024

(54) MEANS AND METHODS APPLYING sFlt-1/PlGF OR ENDOGLIN/PlGF RATIO TO RULE OUT ONSET OF PREECLAMPSIA WITHIN A CERTAIN TIME PERIOD

(71) Applicant: Roche Diagnostics Operations, Inc., Indianapolis, IN (US)

(72) Inventors: Martin Hund, Horw (CH); Maria Schoedl, Baierbrunn (DE)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 0 days.

(21) Appl. No.: 14/576,944

(22) Filed: Dec. 19, 2014

(65) Prior Publication Data

US 2015/0338415 A1    Nov. 26, 2015

Related U.S. Application Data

(63) Continuation of application No. PCT/EP2013/063115, filed on Jun. 24, 2013.

(30) Foreign Application Priority Data

Jun. 27, 2012  (EP) .................................... 12173886
Sep. 7, 2012   (EP) .................................... 12183508

(51) Int. Cl.
*G01N 33/68*    (2006.01)
*G16H 50/30*    (2018.01)
*G16H 50/70*    (2018.01)

(52) U.S. Cl.
CPC ........... *G01N 33/689* (2013.01); *G16H 50/30* (2018.01); *G16H 50/70* (2018.01); *G01N 2333/475* (2013.01); *G01N 2333/515* (2013.01); *G01N 2333/71* (2013.01); *G01N 2333/912* (2013.01); *G01N 2800/368* (2013.01)

(58) Field of Classification Search
CPC .. G16H 50/30; G16H 50/70; G01N 2333/475; G01N 2333/71; G01N 2800/368
See application file for complete search history.

(56) References Cited

U.S. PATENT DOCUMENTS

| | | | |
|---|---|---|---|
| 5,744,305 A | 4/1998 | Fodor et al. | |
| 7,727,733 B2 | 6/2010 | Buhimschi et al. | |
| 2003/0108973 A1* | 6/2003 | Gatto-Menking | G01N 33/582 435/7.93 |
| 2003/0175686 A1* | 9/2003 | Rose .................. | G01N 33/5767 435/5 |
| 2004/0121343 A1* | 6/2004 | Buechler ............. | C12Q 1/6883 435/6.14 |
| 2005/0106652 A1* | 5/2005 | Massey ................. | G01N 33/76 435/6.12 |
| 2006/0067937 A1* | 3/2006 | Karumanchi ...... | A61K 31/4439 424/145.1 |
| 2008/0213794 A1* | 9/2008 | Thadhani ............. | G01N 33/689 435/7.1 |
| 2009/0068683 A1* | 3/2009 | Garovic ............. | G01N 33/6893 435/7.21 |
| 2009/0176247 A1 | 7/2009 | Bashirians et al. | |
| 2010/0010041 A1* | 1/2010 | Stanton .................. | A61P 25/28 546/239 |
| 2010/0041680 A1* | 2/2010 | Rivkin ................ | C07D 471/10 544/323 |
| 2011/0280863 A1 | 11/2011 | Buhimschi et al. | |
| 2011/0294227 A1 | 12/2011 | Ahola et al. | |
| 2012/0164669 A1* | 6/2012 | Hess .................. | G01N 33/6893 435/7.94 |

FOREIGN PATENT DOCUMENTS

| | | | | |
|---|---|---|---|---|
| EP | 1804836 | B1 | 11/2010 | |
| EP | 2311865 | A1 * | 4/2011 | ....... G01N 33/57484 |
| EP | 1952156 | B1 | 5/2011 | |
| EP | 2383579 | A1 * | 11/2011 | ....... G01N 33/57488 |
| EP | 2490027 | A1 | 8/2012 | |
| WO | 2004/008946 | A2 | 1/2004 | |
| WO | 2005/077007 | A2 | 8/2005 | |

(Continued)

OTHER PUBLICATIONS

BabyCenter, Second trimester prenatal visits, retrieved from https://web.archive.org/web/20080202144701/http://www.babycenter.com/0_secondtrimesterprenatalvisits_9345.bc? on Mar. 27, 2017, 2008, 2 pages.*
McElrath TF, Lim K-H, Pare E, et al. Longitudinal evaluation of predictive value for preeclampsia of circulating angiogenic factors throughpregnancy. Am J Obstet Gynecol 2012;207:407.e1-7. (Year: 2012).*
Wagner (American Family Physician 2004 70: 2317-2324). (Year: 2004).*
Levine (New England Med. 2006 355:992-1005) (Year: 2006).*
Schiettecatte (Clin. Biochemistry 2010 vol. 43: 768-770) (Year: 2010).*

(Continued)

*Primary Examiner* — Changhwa J Cheu
(74) *Attorney, Agent, or Firm* — Taft Stettinius & Hollister LLP

(57) ABSTRACT

The present invention concerns the field of diagnostic assays for prenatal diagnosis of preeclampsia. In particular, it relates to a method for diagnosing whether a pregnant subject is not at risk for preeclampsia within a short window of time comprising a) determining the amount of at least one angiogenesis biomarker selected from the group consisting of sFlt-1, Endoglin and PlGF in a sample of said subject, and b) comparing the amount with a reference, whereby a subject being not at risk for developing preeclampsia within a short period of time is diagnosed if the amount is identical or decreased compared to the reference in the cases of sFlt-1 and Endoglin and identical or increased in the case of PlGF, wherein said reference allows for making the diagnosis with a negative predictive value of at least about 98%. Further contemplates are devices and kits for carrying out said method.

3 Claims, 16 Drawing Sheets

(56) References Cited

FOREIGN PATENT DOCUMENTS

| WO | 2006/034507 | A2 | 3/2006 | |
|---|---|---|---|---|
| WO | WO 2011080170 | A1 * | 7/2011 | ........... G01N 33/689 |
| WO | 2011/128357 | A3 | 10/2011 | |

OTHER PUBLICATIONS

Lapaire (Euro J Obstetrics . & Gynecology Reproductive Biol. 2010 151:122-129). (Year: 2010).*

Brown (JAMA 1999 282:1447-1452). (Year: 1999).*

Lee, Wes-Chung, Selecting diagnostic tests for ruling out or ruling in disease: the use of the Kullback-Leibler distance, International Journal of Epidemiology, 1999, pp. 521-525, vol. 28, No. 3.

Vitoratos, N. et al., Molecular Mechanisms of Preeclampsia, Journal of Pregnancy, 2012, 5 pp., Article ID 298343.

Aggarwal, P.K. et al., The relationship between circulating endothelin-1, soluble fms-like tyrosine kinawe-1 and soluble endoglin in preeclampsia, Journal of Human Hypertension, 2012, pp. 236-241, vol. 26.

Guidelines of the Federal Joint Committee on Medical Care During Pregnancy and After Delivery, 2007, 27 pp., Köln, Germany.

Kim, Shin-Young et al., Increased sFlt-1 to PlGF Ratio in Women Who Subsequently Develop Preeclampsia, Journal of Korean Medical Science, 2007, pp. 873-877, vol. 22.

Levine, Richard J. et al., Circulating Angiogenic Factors and the Risk of Preeclampsia, The New England Journal of Medicine, 2004, pp. 672-683, vol. 350.

Masuyama, Hisashi et al., Correlation between Soluble Endoglin, Vascular Endothelial Growth Factor Receptor-1, and Adipocytokines in Preeclampsia, The Journal of Clinical Endocrinology & Metabolism, 2007, pp. 2672-2679, vol. 92, No. 7.

Noori, Muna et al., Prospective Study of Placental Angiogenic Factors and Maternal Vascular Function Before and After Preeclampsia and Gestational Hypertension, Circulation, 2010, pp. 478-487, vol. 122.

Rana, S. et al., Angiogenic factors and risk of preeclampsia related adverse outcomes in twin pregnancies, Abstract PP059, Pregnancy Hypertension: An International Journal of Women's Cardiovascular Health 2, 2012, pp. 273-274.

Schiettecatte, J. et al., Multicenter evaluation of the first automated Elecsys sFlt-1 and PlGF assays in normal pregnancies and preeclampsia, Clinical Biochemistry, 2010, pp. 768-770, vol. 43.

Schoofs, K et al., Prediction of preeclampsia with the sFlt-1/PLGF ratio: impact of the scope of repeated measurements, Abstract PP051, Pregnancy Hypertension: An International Journal of Women's Cardiovascular Health 2, 2012, p. 269.

Sibai, Baha M., Biomarker for hypertension-preeclampsia: are we close yet?, American Journal of Obstetrics and Gynecology, 2007, pp. 1-2, vol. 197, Issue 1.

International Search Report issued Jul. 31, 2013, in Application No. PCT/EP2013/063115, 4 pages.

Albaiges, Gerard et al., "One-Stage Screening for Pegnancy Complications by Color Doppler Assessment of the Uterine Arteries at 23 Weeks' Gestation," Obstetrics & Gynecology, 2000, pp. 559-564, vol. 96, No. 4.

Benton, Samantha J. et al., "Angiogenic factors as diagnostic tests for preeclampsia: a performance comparison between two commercial immunoassays," American Journal of Obstetrics & Gynecology, 2011, pp. 1.e1-1.e8, vol. 205.

Berg, Cynthia J. et al., "Pregnancy-Related Mortality in the United States, 1998 to 2005," Obstetrics & Gynecology, 2010, pp. 1302-1309, vol. 116, No. 6.

Chaiworapongsa, Tinnakorn et al., "Maternal plasma concentrations of angiogenic/anti-angiogenic factors are of prognostic value in patients presenting to the obstetrical triage area with the suspicion of preeclampsia," The Journal of Maternal-Fetal and Neonatal Medicine, 2011, pp. 1187-1207, vol. 24, No. 10.

Chen, Qian et al., "Predictive value of soluble vascular endothelial growth factor receptor 1 for preeclampsia in second-trimester," Chinese Journal of Obstetrics and Gynecology, 2007, pp. 161-164, vol. 42, No. 3.

Chen, Yu, "Novel Angiogenic Factors for Predicting Preeclampsia: sFlt-1, PlGF, and Soluble Endoglin," The Open Chemical Chemistry Journal, 2009, pp. 1-6, No. 2.

Crispi, E et al., "Predictive value of angiogenic factors and urinary artery Doppler for early- versus late-onset pre-eclampsia and interauterine growth restriction," Ultrasound Obstetrics and Gynecology, 2008, pp. 303-309, vol. 31.

De Vivo, Angonio et al., "Endoglin, PlGF, and sFlt-1 as markers for predicting pre-eclampsia," Acta Obstetrica et Gynecologica, 2008, pp. 837-842, vol. 87.

Diab, Abdalla E. et al., "Angiogenic factors for the prediction of pre-eclampsia in women with abnormal midtrimester uterine artery Doppler velocimetry," International Journal of Gynecology and Obstetrics, 2008, pp. 146-151, vol. 102, No. 2.

"Diagnosis and Treatment of Hypertensive Disorders of Pregnancy," German Society of Gynaecology and Obstetrics Guidelines, Recommendations, Position Statements, 2010, 18 pages (English translation of Leitlinien, Empfehlungen, Stellungnahmen of the Deutsche Gesellschaft für Gynäkologie und Geburtschilfe e.V., Aug. 2008).

Duley, Lelia, "The Global Impact of Pre-eclampsia and Eclampsia," Seminars in Perinatology, 2009, pp. 130-137, vol. 33.

Gilstrap, Larry C. III and Ramin, Susan M., "Diagnosis and Management of Preeclampsia and Eclampsia," ACOG Practice Bulletin, 2002, 9 pages, No. 33.

Grill, Simon et al., "Potential markers of preeclampsia—a review, Reproductive Biology and Endocrinology," 2009, 14 pps., vol. 7, No. 70.

Hagmann, Henning et al., "The Promise of Angiogenic Markers for the Early Diagnosis and Prediction of Preeclampsia," Clinical Chemistry, 2012, 9 pages, vol. 58, No. 5.

Kendall, Richard L. et al., "Identification of a Natural Soluble Form of the Vascular Endothelial Growth Factor Receptor, FLT-1, and its Heterodimerization with KDR," Biochemical and Biophysical Research Communications, 1996, pp. 324-328, vol. 226.

Kusanovic, Juan Pedro et al., "A prospective cohort study of the value of maternal plasma concentrations of angiogenic and anti-angiogenic factors in early pregnancy and midtrimester in the identification of patients destined to develop preeclampsia," The Journal of Maternal-Fetal and Neonatal Medicine, 2009, pp. 1021-1038, vol. 22, No. 11.

Lim, Ji Hyea et al., "Effective Prediction of Preeclampsia by a Combined Ratio of Antiogenesis-Related Factors," Obstetrics & Gynecology,: pp. 1403-1409, vol. 111, No. 6, 2008.

Maglione, Domenico et al., "Two alternative mRNAs coding for the antiogenic factor, placenta growth factor (PlGF), are transcribed from a single gem of chromosome 14," Oncogene, 1993, pp. 925-931, vol. 8.

National Collaborating Center for Women's and Children's Heath, "Hypertension in pregnancy, the management of hypertensive disorders during pregnancy," Commission by the National Institute for Health and Clinical Excellence, 2010, 295 pages.

Needleman, Saul B. and Wunsch, Christian D., "A General Method Applicable to the Search for Similarities in the Amino Acid Sequence of Two Proteins," Journal of Molecular Biology, 1970, pp. 443-453, vol. 48.

Nolan, John P. and Sklar, Larry A., "Suspension array technology: evolution of the flat-array paradigm," Trends in Biotechnology, 2002, pp. 9-12, vol. 20, No. 1.

Ohkuchi, Akihide et al., "Evaluation of a new and automated electrochemiluminescence immunoassay for plasma sFlt-1 and PlGF levels in women with preeclampsia," Hypertension Research, 2010, pp. 422-427, vol. 33, No. 5.

Ohkuchi, Akihide et al., "Threshold of Soluble Fms-Like Tyrosine Kinase 1/Placental Growth Factor Ratio for the Imminent Onset of Preeclampsia," Hypertension, 2011, pp. 859-866, vol. 58.

Pearson, William R. and Lipman, David J., "Improved tools for biological sequence comparison," Proceedings of the National Academy of Sciences USA, 1988, pp. 2444-2448, vol. 85.

(56) References Cited

OTHER PUBLICATIONS

Rana, Sarosh et al., "Sequential Changes in Antiangiogenic Factors in Early Pregnancy and Risk of Developing Preeclampsia," Hypertension, 2007, pp. 137-142, No. 50.

Smith, Temple F. and Waterman, Michael S., "Comparison of Biosequences," Advances in Applied Mathematics, 1981, pp. 482-489, vol. 2.

Stepan, Holger et al., "Circulatory soluble endoglin and its predictive value for preeclampsia in second-trimester pregnancies with abnormal uterine perfusion," American Journal of Obstetrics & Gynecology, 2008, pp. 175.e1-175.e6, vol. 198.

Stepan, Holger et al., "Predictive Value of Maternal Angiogenic Factors in Second Trimester Pregnancies With Abnormal Uterine Perfusion," Hypertension, 2007, pp. 818-824, vol. 49.

Stepan, H. et al., "Use of Angiogenic Factors (sFlt-1/PlGF Ratio) to Confirm the Diagnosis of Preeclampsia in Clinical Routine: First Experience," Z Geburtsch Neonatol, 2010, pp. 234-238, vol. 214.

Sunderji, Shiraz et al., "Automated assays for sVEGF R1 and PlGF as an aid in the diagnosis of preterm preeclampsia: a prospective clinical study," American Journal of Obstetrics & Gynecology, 2010, pp. 40.e1-40.e7, vol. 202.

Verlohren, Stefan et al., "An Automated method for the determination of the sFlt-1/PlGF ratio in the assessment of preeclampsia," American Journal of Obstetrics & Gynecology, 2010, pp. 161.e1-161.e11, vol. 202.

Verlohren, Stefan et al., "The sFlt-1/PlGF ratio in different types of hypertensive pregnancy disorders and its prognostic potential in preeclamptic patients," American Journal of Obstetrics & Gynecology, 2012, pp. 58.e1-58.e8, vol. 206.

Verlohren, Stefan et al., "Angiogenic growth factors in the diagnosis and prediction of pre-eclampsia," Clinical Science, 2012, pp. 43-52, vol. 122.

Young, Brett et al., "The use of angiogenic biomarkers to differentiate non-HELLP related thrombocytopenia from HELLP syndrome," The Journal of Maternal-Fetal and Neonatal Medicine, 2010, pp. 366-370, vol. 23, No. 5.

Zweig, Mark H. and Campbell, Gregory, "Receiver-Operating Characteristic (ROC) Plots: A Fundamental Evaluation Tool in Clinical Medicine," Clinical Chemistry, 1993, pp. 561-577, vol. 39, No. 4.

Zeisler et al., Soluble fms-like tyrosine kinase-1 to placental growth factor ratio: ruling out pre-eclampsia for up to 4 weeks and value of retesting; Ultrasound Obstet Gynecol, 2019, vol. 53, pp. 367-375.

Lapaire et al., The preeclampsia biomarkers soluble fms-like tyrosine kinase-1 and placental growth factor: current knowledge, clinical implications and future application; European Journal of Obstetrics & Gynecology and Reproductive Biology; 2010, vol. 151, pp. 122-129.

Rana et al., Angiogenic Factors and the Risk of Adverse Outcomes in Women With Suspected Preeclampsia; Vascular Medicine; 15-pages, 2012.

\* cited by examiner

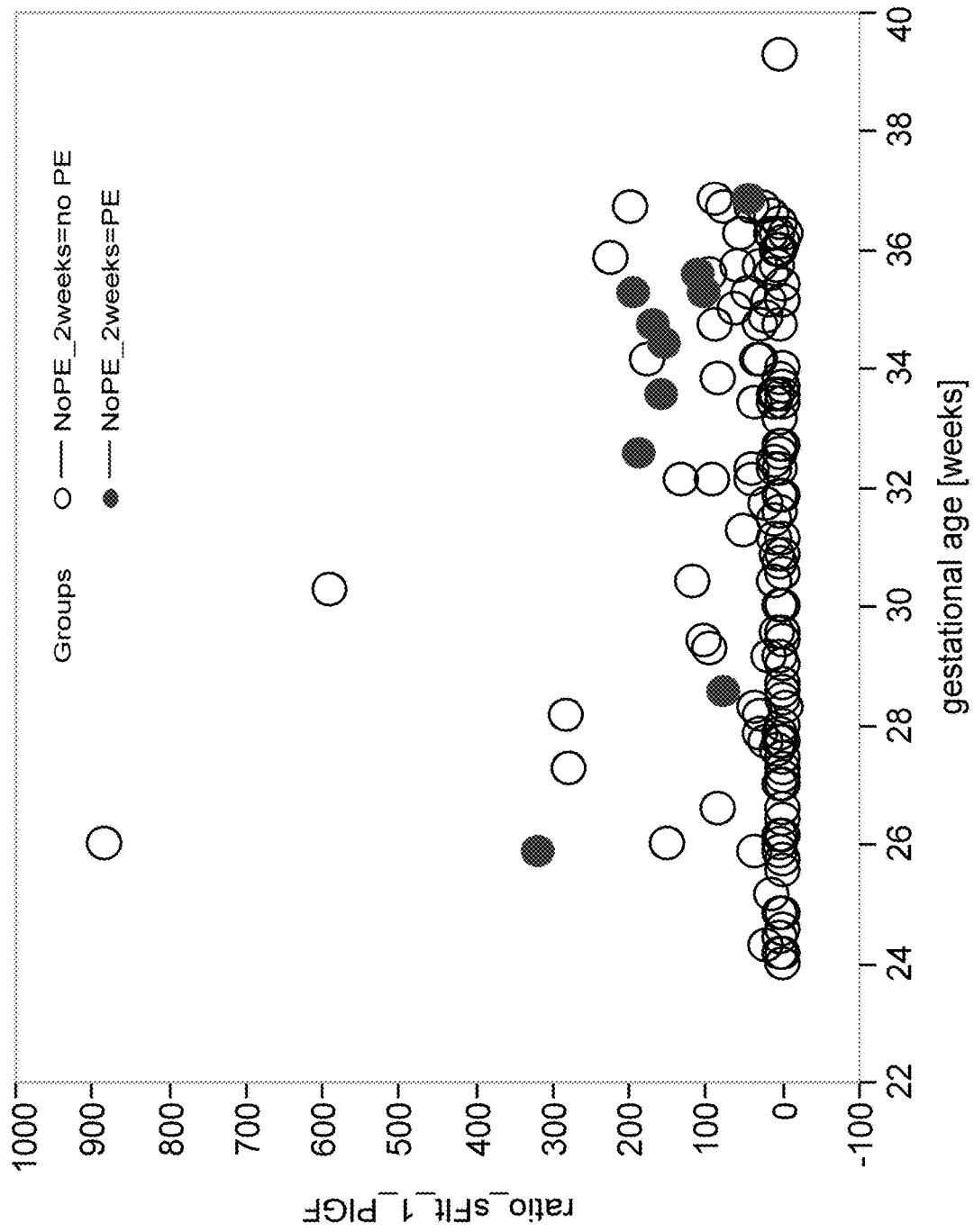

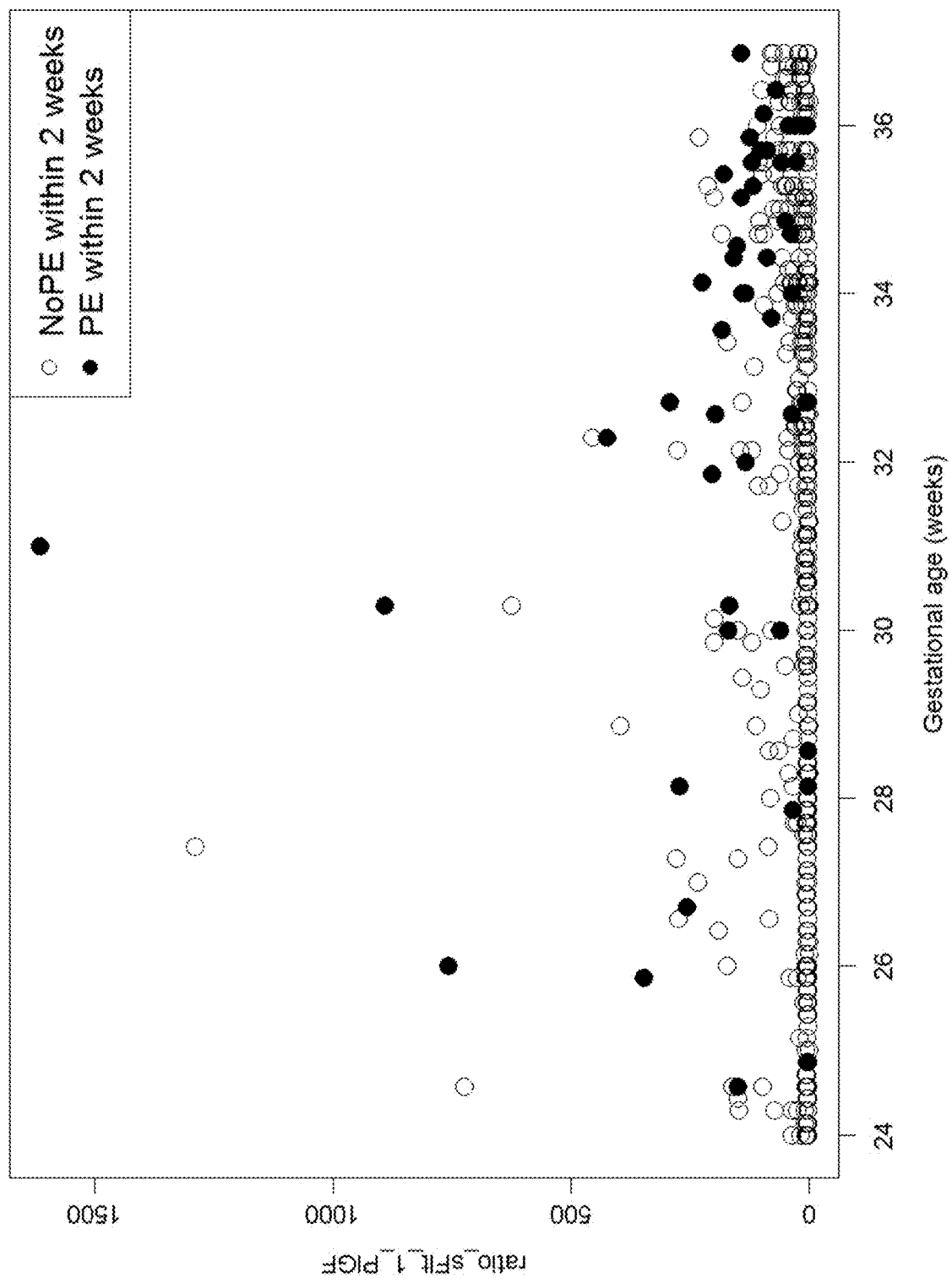

MEANS AND METHODS APPLYING sFlt-1/PlGF OR ENDOGLIN/PlGF RATIO TO RULE OUT ONSET OF PREECLAMPSIA WITHIN A CERTAIN TIME PERIOD

RELATED APPLICATIONS

This application is a continuation of International Application No. PCT/EP2013/063115 filed Jun. 24, 2013, which claims priority to European Application No. 12173886.8 filed Jun. 27, 2012, and European Application No. 12183508.6 filed Sep. 7, 2012, the disclosures of which are hereby incorporated by reference in their entirety.

FIELD OF THE INVENTION

The present invention concerns the field of diagnostic assays for prenatal diagnosis of preeclampsia. In particular, it relates to a method for diagnosing whether a pregnant subject is not at risk for preeclampsia within a short window of time comprising a) determining the amount of at least one angiogenesis biomarker selected from the group consisting of sFlt-1, Endoglin and PlGF in a sample of said subject, and b) comparing the amount with a reference, whereby a subject being not at risk for developing preeclampsia within a short period of time is diagnosed if the amount is identical or decreased compared to the reference in the cases of sFlt-1 and Endoglin and identical or increased in the case of PlGF, wherein said reference allows for making the diagnosis with a negative predictive value of at least about 98%. Further contemplated are devices and kits for carrying out said method.

BACKGROUND

Pregnancy may be complicated in different ways, it is on one hand associated with pregnancy related mortality of the pregnant woman and, on the other hand, also associated with increased morbidity and mortality of the newborn. Maternal mortality at a rate of 14.5 per 100.000 live births, is more frequent in pregnant women above the age of 39 years and may be caused by hemorrhage, thrombotic pulmonary embolism, infections, cardiomyopathy and cardiovascular and noncardiovascular conditions as well as hypertensive disorders among which preeclampsia is the most frequent (Berg 2010, Obstetrics and Gynecology: 116: 1302-1309). Preeclampsia complicates approximately 2 to 8 percent of all pregnancies and is a major contributor to maternal and fetal mortality worldwide (Duley 2009, Semin Perinatol: 33: 130-37). Preeclampsia is generally defined as pregnancy associated or induced hypertension and proteinuria with onset after week 20 of gestation. Hypertension is defined in this context as blood pressure of 140 mmHg (systolic) and/or 90 mmHg (diastolic) or more at two independent measurements, wherein said two measurements have been made at least 6 hours apart. Proteinuria is indicated by 300 mg protein or more in a 24-hour urine sample. However, the definitions of preeclampsia are subject to debate and can differ among societies. Details are also found in the standard text books of medicine and the Guidelines of the various clinical societies, e.g., ACOG Practice Bulletin, Clinical Management Guidelines for Obstetrician—Gynecologists, no.: 33, January 2002 or Leitlinien, Empfehlungen, Stellungnahmen of the Deutschen Gesellschaft für Gynäkologie and Geburtshilfe e.V., August 2008, NICE Clinical Guideline Hypertension in pregnancy: the management of hypertensive disorders during pregnancy, August 2010 (revised reprint January 2011).

The pathogenesis of preeclampsia is largely unknown. It is believed, however, to be caused by disturbed placental function associated with impaired remodelling of the spiral artery. Flow defects occurring in the process of the development of preeclampsia are associated with ischemia which ultimately results in the release of anti-angiogenic factors into the circulation such as sFlt-1 and Endoglin.

The sole treatment of preeclampsia until today is the termination of pregnancy either by premature vaginal or caesarean delivery. As discussed above maternal risks and fetal viability are significantly impaired in case of preeclampsia before gestational week 34. Accordingly, attempts should be made to delay delivery and to thereby improve survival of the newborn.

The early and reliable diagnosis of preeclampsia and, in particular, the rule-out of preeclampsia which occurs as early as 20 to 40 weeks of gestation is decisive for clinical management of the disease. It will be understood that pregnant females suffering from preeclampsia need special care such as close monitoring, supportive therapeutic measures and, in the case of progression into severe preeclampsia, hospitalization in specialized hospitals having maternal fetal intensive care units (MFICUs). In particular, the early-onset-preeclampsia is challenging for the clinicians in light of the severe side-effects and the adverse outcomes associated therewith. Moreover, the early and reliable diagnosis of preeclampsia as well as the prediction of preeclampsia is decisive for the planning of preventive or therapeutic intervention studies (Ohkuchi 2011, Hypertension 58: 859-866). On the other hand, patients belonging into a risk group for which an increased risk for preeclampsia within a certain time window can be ruled-out, shall need less special care and, most often, can be treated ambulant (out patient setting).

Doppler ultrasonography has been applied to identify patients with abnormal uterine perfusion and those patients exhibiting abnormal perfusion identified by Doppler ultrasonography have been suggested to be at risk of developing preeclampsia, eclampsia and/or HELLP syndrome (Stepan 2007, Hypertension, 49: 818-824; Stepan 2008, Am J Obstet Gynecol 198: 175.e1-1). A drawback of Doppler ultrasonography is, however, that highly specialised medical practitioners are required for carrying out and evaluating the results.

Recently, angiogenic factors and anti-angiogenic factors have been suggested to be indicators for preeclampsia. In particular, Placental growth factor (PlGF), Endoglin and the soluble fsm-like tyrosine kinase 1 (sFlt-1) have been reported to be altered in patients suffering from preeclampsia. Besides of the report of the individual factors and their changes in healthy individuals and patients suffering from preeclampsia or patients being at risk of developing preeclampsia (see, e.g., Rana 2007, Hypertension 50: 137-142; WO2004/008946), ratios of sFlt-1 and PlGF or Endoglin and PlGF have been reported as diagnostic or prognostic parameters (see Young 2010, J Matern Fetal Neonatal Med 23(5): 366-370; Hagmann 2012, Clinical Chemistry 58(5): 1-9).

A single ratio for sFlt-1 and PlGF has been reported as a prognostic rule-in factor for preeclampsia at early pregnancy (Crispi 2008, Ultrasound Obstet Gynecol 31: 303-309). Moreover, individual ratios of sFlt-1 and PlGF at different time points of pregnancy have been individually correlated with a risk for preeclampsia (DeVivo 2008, Acta Obstetricia et Gynecologica 87: 837-842; Ohkuchi 2011, loc cit.;

Kusanovic 2009, J of Maternal-Fetal and Neonatal Medicine 22(11): 1021-1038, Chaiworapongsa 2011, J Maternal-Fetal and Neonatal Medicine 24(10): 1187-1207; Benton 2011, American Journal of Obstetrics & Gynecology 205: 1.e1). Moreover, the degree of the changes has been investigated with respect to the prognosis of preeclampsia (Kusanovic 2009, loc cit.) or the risk for an imminent delivery (Verlohren 2012, American Journal of Obstetrics & Gynecology 206(1): 58.e1-58.e8).

The aforementioned prior art, however, mainly concerns the rule-in diagnosis of imminent preeclampsia or prediction thereof. Less is known with respect to ruling-out imminent preeclampsia in a certain time window. There are rather general reports suggesting that based on a certain ratio of sFLt-1 and PlGF imminent preeclampsia at the day of patient presentation could be ruled out (Stepan 2010, Z Geburtsh Neonatol 214: 234-238).

However, a reliable assay for ruling-out preeclampsia within a certain time period in an apparently healthy pregnant female is not yet available but nevertheless highly desired.

The technical problem underlying the present invention can be seen as the provision of means and methods for complying with the aforementioned needs. The technical problem is solved by the embodiments characterized in the claims and herein below.

SUMMARY OF THE INVENTION

The present invention relates to a method for diagnosing whether a pregnant subject is not at risk for preeclampsia (i.e. ruling out preeclampsia) within a short window of time comprising:
a) determining the amount of at least one angiogenesis biomarker selected from the group consisting of sFlt-1, Endoglin and PlGF in a sample of said subject; and
b) comparing the amount with a reference, whereby a subject being not at risk for developing preeclampsia within a short period of time is diagnosed if the amount is identical or decreased compared to the reference in the cases of sFlt-1 and Endoglin and identical or increased in the case of PlGF, wherein said reference allows for making the diagnosis with a negative predictive value of at least about 98%.

The method of the present invention, preferably, is an ex vivo method. Moreover, it may comprise steps in addition to those explicitly mentioned above. For example, further steps may relate to sample pre-treatments or evaluation of the results obtained by the method. The method may be carried out manually or assisted by automation. Preferably, step (a), and/or (b) may in total or in part be assisted by automation, e.g., by a suitable robotic and sensory equipment for the determination in step (a), a computer-implemented calculation algorithm on a data processing device and/or comparison and/or diagnosis algorithm on a data processing device in step (b).

The term "preeclampsia" as used herein refers to a medical condition which is characterized by hypertension and proteinuria. Preeclampsia occurs in pregnant female subjects and the hypertension is also referred to as pregnancy-induced hypertension. Preferably, the pregnancy-induced hypertension is identified to be present in a subject by two blood pressure measurements of 140 mmHg (systolic) and/or 90 mmHg (diastolic) or more, wherein said two measurements have been made at least 6 hours apart. Proteinuria is, preferably, identified to be present by 300 mg protein or more in a 24-hour urine sample. Preeclampsia may progress to eclampsia, a life-threatening disorder characterized by the appearance of tonic-clonic seizures or coma conditions. Symptoms associated with severe preeclampsia are oligouria of less than 500 ml within 24 hours, cerebral or visual disturbance, pulmonary edema or cyanosis, epigastric—or right upper quadrant—pain, impaired liver function, thrombocytopenia, fetal growth restriction. Subjects suffering from preeclampsia with hepatic involvement may further develop the HELLP syndrome. Accordingly, a subject according to the invention which is at risk of developing preeclampsia, preferably, is also potentially at risk of developing the HELLP syndrome. The HELLP syndrome is associated with a high risk of adverse outcomes such as placental abruption, renal failure, subcapsular hepatic hematoma, recurrent preeclampsia, preterm delivery, or even materal and/or fetal death. Further details of preeclampsia and the accompanying symptoms as well as the follow up diseases such as HELLP syndrome or eclampsia are to be found in standard text books of medicine or Guidelines of the relevant medical societies. Details can be found, e.g., in ACOG Practice Bulletin, Clinical Management Guidelines for Obstetrician—Gynecologists, no.: 33, January 2002 or Leitlinien, Empfehlungen, Stellungnahmen of the Deutschen Gesellschaft für Gynäkologie und Geburtshilfe e.V., August 2008, NICE Clinical Guideline Hypertension in pregnancy: the management of hypertensive disorders during pregnancy, August 2010 (revised reprint January 2011). Preeclampsia occurs in up to 10% of pregnancies usually in the second or third trimester. However, some females develop preeclampsia as early as in week 20 of gestation.

Within week 20 to 34 of gestation, preeclampsia is also called early-onset-preeclampsia while preeclampsia which occurs after week 34 of gestation is also termed late-onset-preeclampsia. It will be understood that the early-onset-preeclampsia, usually, is accompanied by more severe side-effects and adverse outcomes compared to the usually relatively mild late-onset-preeclampsia.

The phrase "not at risk for developing preeclampsia" refers to a pregnant subject which will not develop preeclampsia within a prognostic time window in the future with a statistically significantly increased likelihood compared to a pregnant subject which is at risk for developing preeclampsia or compared to the prevalence for preeclampsia within a population including the subject to be analysed.

The term "subject" as used herein relates to animals, preferably mammals, and, more preferably, humans. The subject according to the present invention shall be a pregnant subject, i.e. a pregnant female. Preferably, the subject according to the present invention shall not suffer from manifest preeclampsia, eclampsia or HELLP syndrome. Preferably, the subject according to the present invention is a subject which has been identified to have abnormal uterine perfusion and, more preferably, may be a subject which has been identified to be at risk for developing preeclampsia, eclampsia and/or HELLP syndrome by other diagnostic techniques already. More preferably, the subject has been identified to be at risk for developing preeclampsia, eclampsia and/or HELLP syndrome by abnormal uterine Doppler ultrasonography results. Preferably, the Doppler ultrasonography has been performed transabdominal (see, e.g., Albaiges 2000, Obstet Gynecol 96: 559-564). In particular, the pulsatility indices (PI) of the uterine arteries may be measured and a mean for both those arteries (mPI-UtA) shall be calculated and can be compared with thresholds that allow distinguishing between normal and abnormal results.

More preferably, the pregnant subject according to the present invention is between about week 20 and about week 40 of gestation, preferably, between about week 24 and about week 40 of gestation. Accordingly, the preeclampsia to be ruled out by the present method of the invention may be early-onset preeclampsia or late-onset preeclampsia depending on the week of gestation when the sample has been taken from the subject.

BRIEF DESCRIPTION OF THE FIGURES

FIG. 2A shows the ratio of sFlt-1/PlGF at different weeks of gestation. Empty circles represent cases where no preeclampsia (PE) has been determined within 2 weeks after the sample has been taken (visit). Grey circles represent cases with preeclampsia (PE). Below a cut-off of 46, no PE cases where detected. (A) n=94, below a cut-off of 46, no PE cases where detected.

FIG. 2B shows the ratio of sFlt-1/PlGF at different weeks of gestation. Empty circles represent cases where no preeclampsia (PE) has been determined within 2 weeks after the sample has been taken (visit). Grey circles represent cases with preeclampsia (PE). Below a cut-off of 46, no PE cases where detected. (B) n=269; below a cut-off of 38, only few PE cases where detected.

DETAILED DESCRIPTION OF THE INVENTION

Figure 1A:
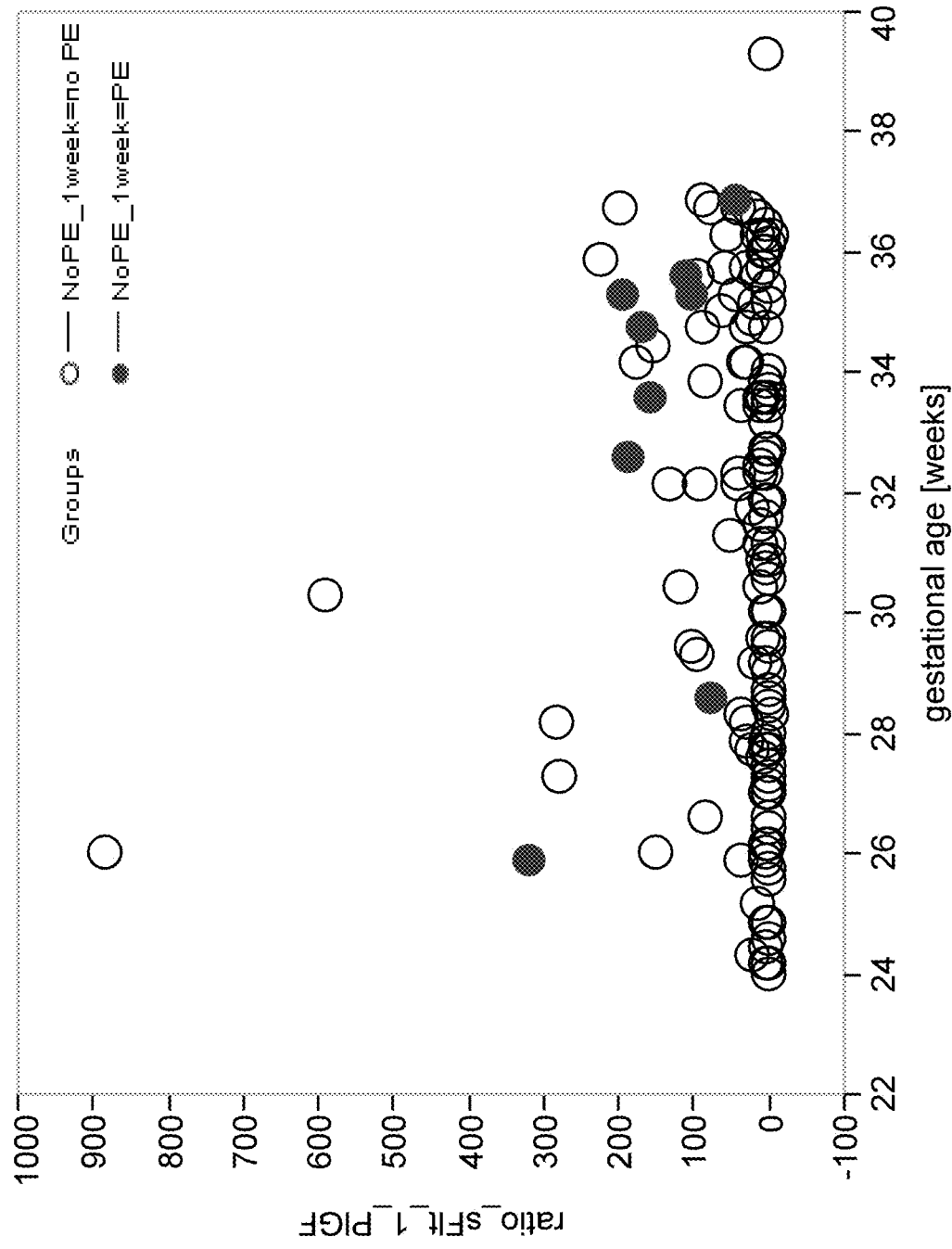
FIG. 1A shows the ratio of sFlt-1/PlGF at different weeks of gestation. Empty circles represent cases where no preeclampsia (PE) has been determined within 1 week after the sample has been taken (visit), grey circles are cases with preeclampsia (PE). (A) n=94, below a cut-off of 46, no PE cases where detected.
Figure 1B:
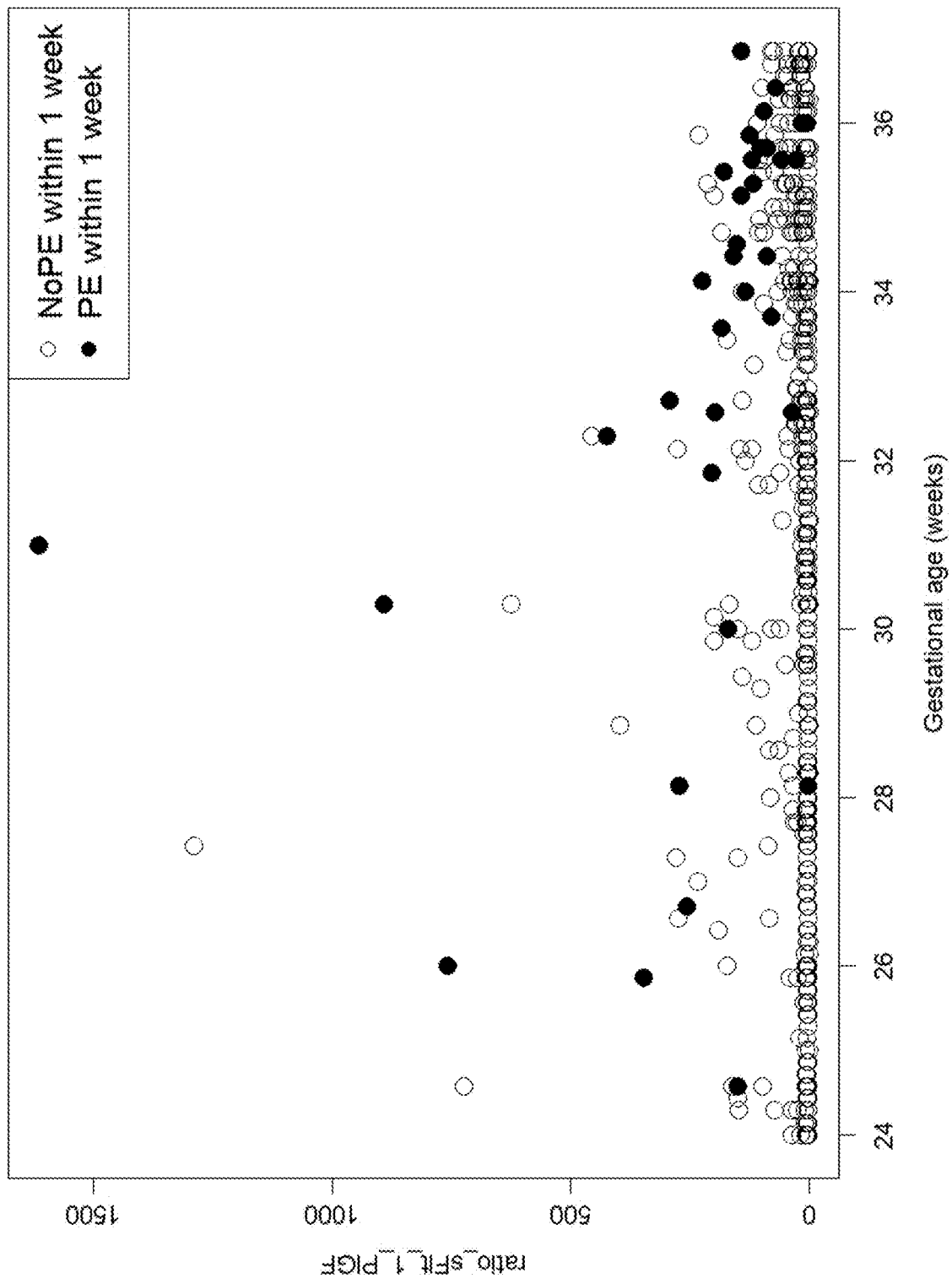
FIG. 1B shows the ratio of sFlt-1/PlGF at different weeks of gestation. Empty circles represent cases where no preeclampsia (PE) has been determined within 1 week after the sample has been taken (visit), grey circles are cases with preeclampsia (PE). (B) n=269; below a cut-off of 38, only few PE cases where detected.
Figure 3A:
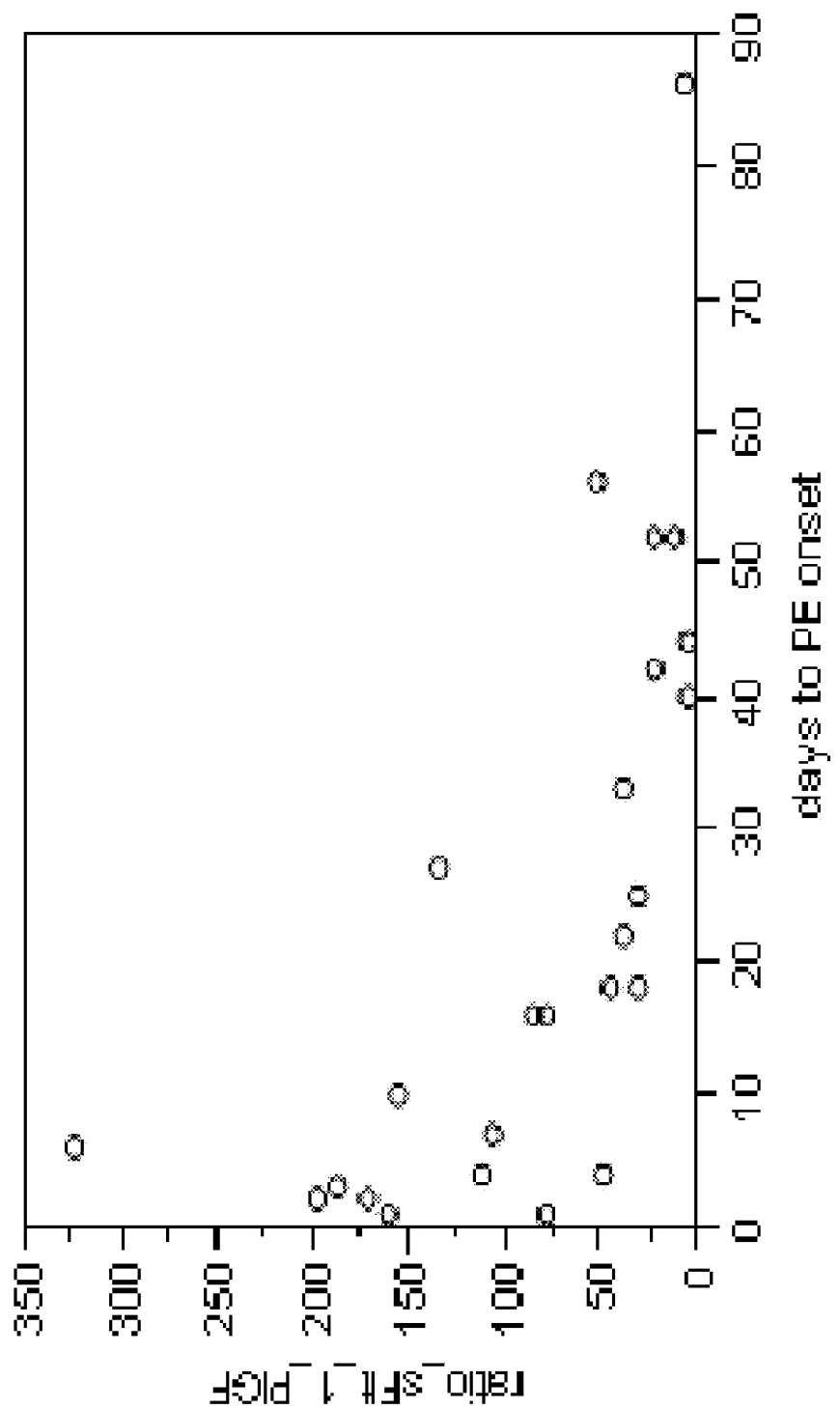
FIG. 3A shows a bivariate distribution analysis of the sFlt-1/PlGF ratios and the days until onset of preeclampsia (PE).
Figure 3B:
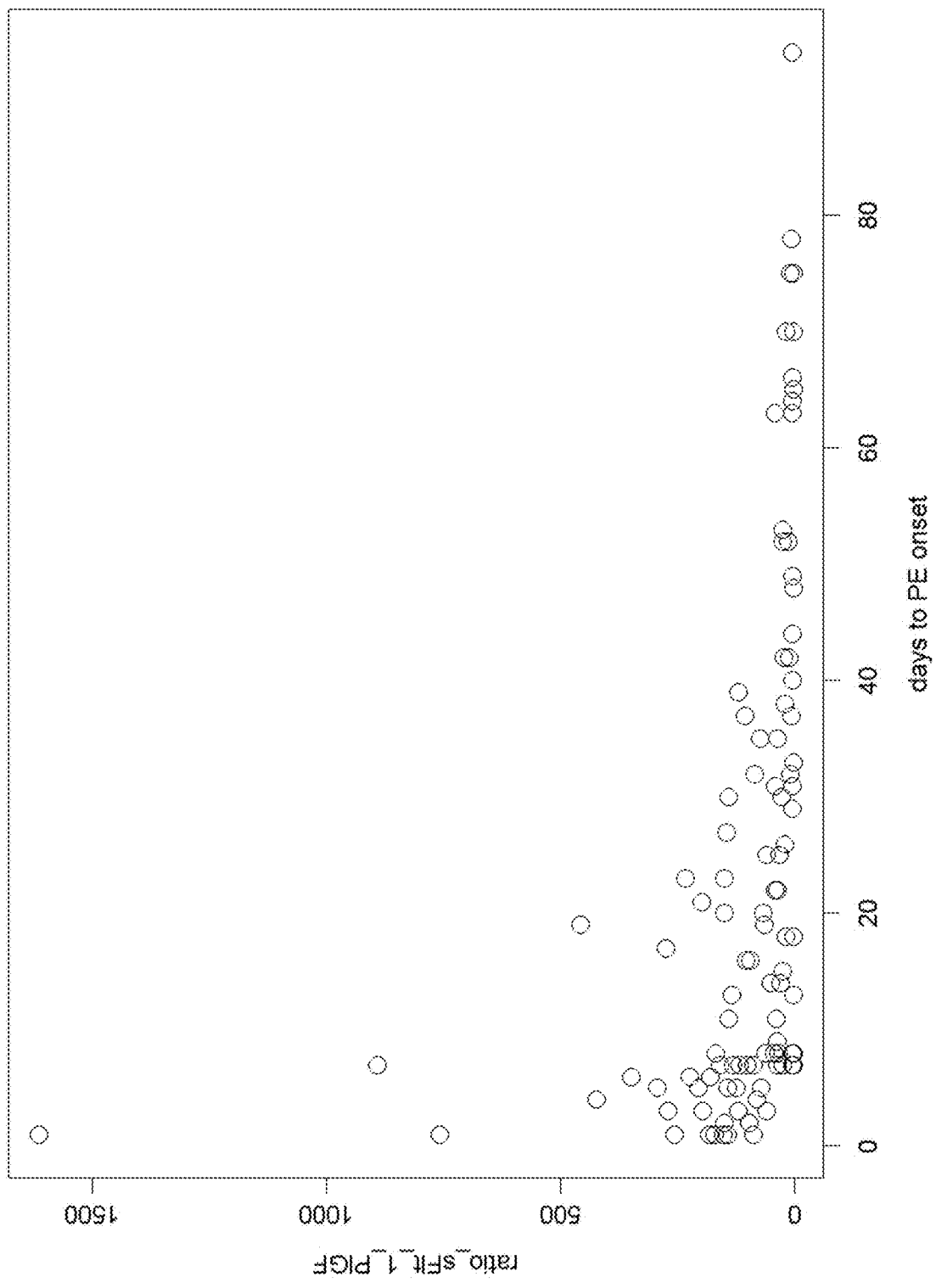
FIG. 3B shows a bivariate distribution analysis of the sFlt-1/PlGF ratios and the days until onset of preeclampsia (PE) same as in (A), but with a larger cohort.

The method of the present invention can be used in routine screening approaches of apparently healthy pregnant subjects. However, the pregnant subject envisaged by the present invention may also belong into a risk group having a higher prevalence for preeclampsia. Pregnant subjects suffering from adiposity, hypertension, autoimmune diseases such as Lupus erythematosus, thrombophilias or diabetes mellitus have an increased prevalence for developing preeclampsia in general. The same applies for subjects which suffered from preeclampsia, eclampsia and/or HELLP syndrome in a previous pregnancy. Furthermore, elderly females who are pregnant for the first time do also exhibit a predisposition for developing preeclampsia. The likelihood for developing preeclampsia, however, is decreasing with the number of pregnancies.

The term "diagnosing" as used herein means assessing whether a subject is not at risk of developing preeclampsia within a short period of time. Preferably, said short period of time is a period of time less than 4 weeks, preferably between about 1 to about 2 weeks. As will be understood by those skilled in the art, such an assessment is usually not intended to be correct for 100% of the subjects to be diagnosed. The term, however, requires that the assessment is correct with a negative predictive value as set forth elsewhere herein for a certain portion of subjects (e.g. a cohort in a cohort study). The risk for developing or not developing preeclampsia in a certain time window in the future can be diagnosed by a test such as the method of the invention with a summary statistic describing the performance of the test with respect to false positive/negative and true positive/negative assessments. A high negative predictive value indicates a high level of confidence in a negative assessment made by a diagnostic test. The negative predictive value can be expressed as the number of true negative results divided by the sum of the true negative results and the false negative results (i.e. all negative outcomes determined by the diagnostic test). In principle, a negative predictive value can be calculated depending on the sensitivity and specificity of a diagnostic test and the prevalence for a disease or condition in certain cohort. Specifically, the negative predictive value is [(specificity) (1−prevalence)]/[(specificity)(1−prevalence)+(1−sensitivity)(prevalence)]. Prevalence predictions can be obtained from cohort studies whereas case control studies may yield sensitivity and/or specificity for the test. In particular, the negative predictive value of the diagnosis established by the method of the present invention shall be at least about 98%, more preferably, at least about 99% and, most preferably, 100%. Further details on statistics are described in standard text books, such as Dowdy and Wearden, Statistics for Research, John Wiley & Sons, New York 1983, or are found elsewhere herein.

The term "sample" refers to a sample of a body fluid, to a sample of separated cells or to a sample from a tissue or an organ. Samples of body fluids can be obtained by well known techniques and include, preferably, samples of blood, plasma, serum, or urine, more preferably, samples of blood, plasma or serum. Tissue or organ samples may be obtained from any tissue or organ by, e.g., biopsy. Separated cells may be obtained from the body fluids or the tissues or organs by separating techniques such as centrifugation or cell sorting. Preferably, cell-, tissue- or organ samples are obtained from those cells, tissues or organs which express or produce the peptides referred to herein.

The term "sFlt-1" as used herein refers to a polypeptide which is a soluble form of the fms-like tyrosine kinase 1. The polypeptide is also referred to as soluble VEGF receptor 1 (sVEGF R1) in the art (see, e.g., Sunderji 2010, Am J Obstet Gynecol 202: 40e1-7). It was identified in conditioned culture medium of human umbilical vein endothelial cells. The endogenous sFlt1 receptor is chromatographically and immunologically similar to recombinant human sFlt1 and binds [125I] VEGF with a comparable high affinity. Human sFlt1 is shown to form a VEGF-stabilized complex with the extracellular domain of KDR/Flk-1 in vitro. Preferably, sFlt1 refers to human sFlt1 as describe in Kendall 1996, Biochem Biophs Res Commun 226(2): 324-328; for amino acid sequences, see, e.g., also Genebank accession numbers P17948, GI: 125361 for human and BAA24499.1, GI: 2809071 for mouse sFlt-1 (Genebank is available from the NCBI, USA. The term also encompasses variants of the aforementioned human sFlt-1 polypeptides. Such variants have at least the same essential biological and immunological properties as the aforementioned sFlt-1 polypeptide. In particular, they share the same essential biological and immunological properties if they are detectable by the same specific assays referred to in this specification, e.g., by ELISA assays using polyclonal or monoclonal antibodies specifically recognizing the said sFlt-1 polypeptides. Moreover, it is to be understood that a variant as referred to in accordance with the present invention shall have an amino acid sequence which differs due to at least one amino acid substitution, deletion and/or addition wherein the amino acid sequence of the variant is still, preferably, at least 50%, 60%, 70%, 80%, 85%, 90%, 92%, 95%, 97%, 98%, or 99% identical with the amino sequence of the specific sFlt-1 polypeptide, preferably over the entire length of the human sFlt-1, respectively. The degree of identity between two amino acid sequences can be determined by algorithms well known in the art. Preferably, the degree of identity is to be determined by comparing two optimally aligned sequences over a comparison window, where the fragment of amino acid sequence in the comparison window may comprise additions or deletions (e.g., gaps or overhangs) as compared to the reference sequence (which does not comprise additions or deletions) for optimal alignment. The percentage is calculated by determining the number of positions at which the identical amino acid residue occurs in both sequences to yield the number of matched positions, dividing the number of matched positions by the total number of positions in the window of comparison and multiplying the result by 100 to yield the percentage of sequence identity. Optimal alignment of sequences for comparison may be conducted by the local homology algorithm disclosed by Smith 1981, Add. APL. Math. 2:482, by the homology alignment algorithm of Needleman 1970, J. Mol. Biol. 48:443, by the search for similarity method of Pearson 1988, Proc. Natl. Acad Sci. (USA) 85: 2444, by computerized implementations of these algorithms (GAP, BESTFIT, BLAST, FAST, PASTA, and TFASTA in the Wisconsin Genetics Software Package, Genetics Computer Group (GCG), 575 Science Dr., Madison, WI), or by visual inspection. Given that two sequences have been identified for comparison, GAP and BESTFIT are preferably employed to determine their optimal alignment and, thus, the degree of identity. Preferably, the default values of 5.00 for gap weight and 0.30 for gap weight length are used.

Variants referred to above may be allelic variants or any other species specific homologs, paralogs, or orthologs. Variants referred to above may be allelic variants or any other species specific homologs, paralogs, or orthologs. Moreover, the variants referred to herein include fragments or subunits of the specific sFlt-1 polypeptides or the aforementioned types of variants as long as these fragments have the essential immunological and biological properties as referred to above. Such fragments may be, e.g., degradation products of the sFlt-1 polypeptides. Variants are deemed to share the same essential biological and immunological properties if they are detectable by the same specific assays referred to in this specification, e.g., by ELISA assays using polyclonal or monoclonal antibodies specifically recognizing the said sFlt-1 polypeptides. A preferred assay is described in the accompanying Examples. Further included are variants which differ due to posttranslational modifications such as phosphorylation or myristylation. sFlt-1 may be detected in bound or free form or as total sFlt-1 amount in a sample.

The term "Endoglin" as used herein refers to a polypeptide having a molecular weight of 180 kDa non-reduced, 95 kDa after reduction and 66 kDa in its reduced and N-deglycosylated form. The polypeptide is capable of forming dimers and binds to TGF-β and TGF-β receptors. Preferably, Endoglin refers to human Endoglin. More preferably, human Endoglin has an amino acid sequence as shown in Genebank accession number AAC63386.1, GI: 3201489. Two Endoglin isoforms, S-Endoglin and L-Endoglin have been described. L-Endoglin consists of total of 633 amino acids with a cytoplasmic tail of 47 amino acids while S-Endoglin consists of 600 amino acids with a cytoplasmic tail of 14 amino acids. Preferably, Endoglin as used herein is soluble Endoglin. Soluble Endoglin as referred to herein is preferably described in EP 1 804 836 B1. Moreover, it is to be understood that a variant as referred to in accordance with the present invention may have an amino acid sequence which differs due to at least one amino acid substitution, deletion and/or addition wherein the amino acid sequence of the variant is still, preferably, at least 50%, 60%, 70%, 80%, 85%, 90%, 92%, 95%, 97%, 98%, or 99% identical with the amino acid sequence of the specific Endoglin. Variants may be allelic variants, splice variants or any other species specific homologs, paralogs, or orthologs. Moreover, the variants referred to herein include fragments of the specific Endoglin or the aforementioned types of variants as long as these fragments have the essential immunological and biological properties as referred to above. Such fragments may be, e.g., degradation products of Endoglin. Variants are deemed to share the same essential biological and immunological properties if they are detectable by the same specific assays referred to in this specification, e.g., by ELISA assays using polyclonal or monoclonal antibodies specifically recognizing the said Endoglin polypeptides. A preferred assay is described in the accompanying Examples. Further included are variants which differ due to posttranslational modifications such as phosphorylation or myristylation. Endoglin may be detected in bound or free form or as total Endoglin amount in a sample.

The term "PlGF (Placental Growth Factor)" as used herein refers to a placenta-derived growth factor which is a polypeptide having 149 amino acids in length and being highly homologous to the platelet-derived growth factor-like region of human vascular endothelial growth factor (VEGF). Like VEGF, PlGF has angiogenic activity in vitro and in vivo. For example, biochemical and functional characterization of PlGF derived from transfected COS-1 cells revealed that it is a glycosylated dimeric secreted protein which is able to stimulate endothelial cell growth in vitro (Maqlione 1993, Oncogene 8(4):925-31). Preferably, PlGF refers to human PlGF, more preferably, to human PlGF having an amino acid sequence as shown in Genebank accession number P49763, GI: 17380553. The term encompasses variants of said specific human PlGF. Such variants have at least the same essential biological and immunological properties as the specific PlGF polypeptide. Variants are deemed to share the same essential biological and immunological properties if they are detectable by the same specific assays referred to in this specification, e.g., by ELISA assays using polyclonal or monoclonal antibodies specifically recognizing the said PlGF polypeptides. A preferred assay is described in the accompanying Examples. Moreover, it is to be understood that a variant as referred to in accordance with the present invention shall have an amino acid sequence which differs due to at least one amino acid substitution, deletion and/or addition wherein the amino acid sequence of the variant is still, preferably, at least 50%, 60%, 70%, 80%, 85%, 90%, 92%, 95%, 97%, 98%, or 99% identical with the amino acid sequence of the specific PlGF polypeptides. The degree of identity between two amino acid sequences can be determined by algorithms well known in the art and described elsewhere herein. Variants referred to above may be allelic variants or any other species specific homologs, paralogs, or orthologs. Moreover, the variants referred to herein include fragments of the specific PLGF polypeptides or the aforementioned types of variants as long as these fragments have the essential immunological and biological properties as referred to above. Such fragments may be, e.g., degradation products or splice variants of the PLGF polypeptides. Further included are variants which differ due to posttranslational modifications such as phosphorylation or myristylation. PlGF may be detected in bound or free form or as total PlGF amount in a sample.

Determining the amount of any peptide or polypeptide referred to in this specification relates to measuring the amount or concentration, preferably, semi-quantitatively or quantitatively. Measuring can be done directly or indirectly. Direct measuring relates to measuring the amount or concentration of the peptide or polypeptide based on a signal which is obtained from the peptide or polypeptide itself and the intensity of which directly correlates with the number of molecules of the peptide present in the sample. Such a signal—sometimes referred to herein as intensity signal—may be obtained, e.g., by measuring an intensity value of a specific physical or chemical property of the peptide or polypeptide. Indirect measuring includes measuring of a signal obtained from a secondary component (i.e. a component not being the peptide or polypeptide itself) or a biological read out system, e.g., measurable cellular responses, ligands, labels, or enzymatic reaction products.

In accordance with the present invention, determining the amount of a peptide or polypeptide can be achieved by all known means for determining the amount of a peptide in a sample. Said means comprise immunoassay devices and methods which may utilize labelled molecules in various sandwich, competition, or other assay formats. Said assays will develop a signal which is indicative for the presence or absence of the peptide or polypeptide. Moreover, the signal strength can, preferably, be correlated directly or indirectly (e.g. reverse-proportional) to the amount of polypeptide present in a sample. Further suitable methods comprise measuring a physical or chemical property specific for the peptide or polypeptide such as its precise molecular mass or NMR spectrum. Said methods comprise, preferably, biosensors, optical devices coupled to immunoassays, biochips, analytical devices such as mass-spectrometers, NMR-analysers, or chromatography devices. Further, methods include micro-plate ELISA-based methods, fully-automated or robotic immunoassays (available for example on Elecsys™ analysers), CBA (an enzymatic Cobalt Binding Assay, available, for example, on Roche-Hitachi™ analysers), and latex agglutination assays (available, for example, on Roche-Hitachi™ analysers).

Preferably, determining the amount of a peptide or polypeptide comprises the steps of (a) contacting a cell capable of eliciting a cellular response the intensity of which is indicative of the amount of the peptide or polypeptide with the said peptide or polypeptide for an adequate period of time, (b) measuring the cellular response. For measuring cellular responses, the sample or processed sample is, preferably, added to a cell culture and an internal or external cellular response is measured. The cellular response may include the measurable expression of a reporter gene or the secretion of a substance, e.g. a peptide, polypeptide, or a small molecule. The expression or substance shall generate an intensity signal which correlates to the amount of the peptide or polypeptide.

Also preferably, determining the amount of a peptide or polypeptide comprises the step of measuring a specific intensity signal obtainable from the peptide or polypeptide in the sample. As described above, such a signal may be the signal intensity observed at an m/z variable specific for the peptide or polypeptide observed in mass spectra or a NMR spectrum specific for the peptide or polypeptide.

Determining the amount of a peptide or polypeptide may, preferably, comprises the steps of (a) contacting the peptide with a specific ligand, (b) preferably removing non-bound ligand, (c) measuring the amount of bound ligand. The bound ligand will generate an intensity signal. Binding according to the present invention includes both covalent and non-covalent binding. A ligand according to the present invention can be any compound, e.g., a peptide, polypeptide, nucleic acid, or small molecule, binding to the peptide or polypeptide described herein. Preferred ligands include antibodies, nucleic acids, peptides or polypeptides such as receptors or binding partners for the peptide or polypeptide and fragments thereof comprising the binding domains for the peptides, and aptamers, e.g. nucleic acid or peptide aptamers. Methods to prepare such ligands are well-known in the art. For example, identification and production of suitable antibodies or aptamers is also offered by commercial suppliers. The person skilled in the art is familiar with methods to develop derivatives of such ligands with higher affinity or specificity. For example, random mutations can be introduced into the nucleic acids, peptides or polypeptides. These derivatives can then be tested for binding according to screening procedures known in the art, e.g. phage display. Antibodies as referred to herein include both polyclonal and monoclonal antibodies, as well as fragments thereof, such as Fv, Fab and F(ab)$_2$ fragments that are capable of binding antigen or hapten. The present invention also includes single chain antibodies and humanized hybrid antibodies wherein amino acid sequences of a non-human donor antibody exhibiting a desired antigen-specificity are combined with sequences of a human acceptor antibody. The donor sequences will usually include at least the antigen-binding amino acid residues of the donor but may comprise other structurally and/or functionally relevant amino acid residues of the donor antibody as well. Such hybrids can be prepared by several methods well known in the art. Preferably, the ligand or agent binds specifically to the peptide or polypeptide. Specific binding according to the present invention means that the ligand or agent should not bind substantially to, i.e. cross-react with, another peptide, polypeptide or substance present in the sample to be analysed. Preferably, the specifically bound peptide or polypeptide should be bound with at least 3 times higher, more preferably at least 10 times higher and even more preferably at least 50 times higher affinity than any other relevant peptide or polypeptide. Non-specific binding may be tolerable, if it can still be distinguished and measured unequivocally, e.g. according to its size on a Western Blot, or by its relatively higher abundance in the sample. Binding of the ligand can be measured by any method known in the art. Preferably, said method is semi-quantitative or quantitative. Further suitable techniques for the determination of a polypeptide or peptide are described in the following.

First, binding of a ligand may be measured directly, e.g. by NMR or surface plasmon resonance. Second, if the ligand also serves as a substrate of an enzymatic activity of the peptide or polypeptide of interest, an enzymatic reaction product may be measured (e.g. the amount of a protease can be measured by measuring the amount of cleaved substrate, e.g. on a Western Blot). Alternatively, the ligand may exhibit enzymatic properties itself and the "ligand/peptide or polypeptide" complex or the ligand which was bound by the peptide or polypeptide, respectively, may be contacted with a suitable substrate allowing detection by the generation of an intensity signal. For measurement of enzymatic reaction products, preferably the amount of substrate is saturating. The substrate may also be labelled with a detectable label prior to the reaction. Preferably, the sample is contacted with the substrate for an adequate period of time. An adequate period of time refers to the time necessary for an detectable, preferably measurable, amount of product to be produced. Instead of measuring the amount of product, the time necessary for appearance of a given (e.g. detectable) amount of product can be measured. Third, the ligand may be coupled covalently or non-covalently to a label allowing detection and measurement of the ligand. Labelling may be done by direct or indirect methods. Direct labelling involves coupling of the label directly (covalently or non-covalently) to the ligand. Indirect labelling involves binding (covalently or non-covalently) of a secondary ligand to the first ligand. The secondary ligand should specifically bind to the first ligand. Said secondary ligand may be coupled with a suitable label and/or be the target (receptor) of tertiary ligand binding to the secondary ligand. The use of secondary, tertiary or even higher order ligands is often used to increase the signal. Suitable secondary and higher order ligands may include antibodies, secondary antibodies, and the well-known streptavidin-biotin system (Vector Laboratories, Inc.). The ligand or substrate may also be "tagged" with one or more tags as known in the art. Such tags may then be targets for higher order ligands. Suitable tags include biotin, digoxygenin, His-Tag, Glutathion-S-Transferase, FLAG, GFP, myc-tag, influenza A virus haemagglutinin (HA), maltose binding protein, and the like. In the case of a peptide or polypeptide, the tag is preferably at the N-terminus and/or C-terminus. Suitable labels are any labels detectable by an appropriate detection method. Typical labels include gold particles, latex beads, acridan ester, luminol, ruthenium, enzymatically active labels, radioactive labels, magnetic labels ("e.g. magnetic beads", including paramagnetic and superparamagnetic labels), and fluorescent labels. Enzymatically active labels include e.g. horseradish peroxidase, alkaline phosphatase, beta-Galactosidase, Luciferase, and derivatives thereof. Suitable substrates for detection include di-amino-benzidine (DAB), 3,3'-5,5'-tetramethylbenzidine, NBT-BCIP (4-nitro blue tetrazolium chloride and 5-bromo-4-chloro-3-indolyl-phosphate, available as ready-made stock solution from Roche Diagnostics), CDP-Star™ (Amersham Biosciences), ECF™ (Amersham Biosciences). A suitable enzyme-substrate combination may result in a coloured reaction product, fluorescence or chemoluminescence, which can be measured according to methods known in the art (e.g. using a light-sensitive film or a suitable camera system). As for measuring the enzymatic reaction, the criteria given above apply analogously. Typical fluorescent labels include fluorescent proteins (such as GFP and its derivatives), Cy3, Cy5, Texas Red, Fluorescein, and the Alexa dyes (e.g. Alexa 568). Further fluorescent labels are available e.g. from Molecular Probes (Oregon). Also the use of quantum dots as fluorescent labels is contemplated. Typical radioactive labels include $^{35}$S, $^{125}$I, $^{32}$P, $^{33}$P and the like. A radioactive label can be detected by any method known and appropriate, e.g. a light-sensitive film or a phosphor imager. Suitable measurement methods according the present invention also include precipitation (particularly immunoprecipitation), electrochemiluminescence (electro-generated chemiluminescence), RIA (radioimmunoassay), ELISA (enzyme-linked immunosorbent assay), sandwich enzyme immune tests, electrochemiluminescence sandwich immunoassays (ECLIA), dissociation-enhanced lanthanide fluoro immuno assay (DELFIA), scintillation proximity assay (SPA), turbidimetry, nephelometry, latex-enhanced turbidimetry or nephelometry, or solid phase immune tests. Further methods known in the art (such as gel electrophoresis, 2D gel electrophoresis, SDS polyacrylamid gel electrophoresis (SDS-PAGE), Western Blotting, and mass spectrometry), can be used alone or in combination with labelling or other detection methods as described above.

The amount of a peptide or polypeptide may be, also preferably, determined as follows: (a) contacting a solid support comprising a ligand for the peptide or polypeptide as specified above with a sample comprising the peptide or polypeptide, (b) preferably removing unbound peptide or polypeptide as well as remaining sample material and (c) measuring the amount peptide or polypeptide which is bound to the support. The ligand is, preferably chosen from the group consisting of nucleic acids, peptides, polypeptides, antibodies and aptamers and is, preferably, present on a solid support in immobilized form. Materials for manufacturing solid supports are well known in the art and include, inter alia, commercially available column materials, polystyrene beads, latex beads, magnetic beads, colloid metal particles, glass and/or silicon chips and surfaces, nitrocellulose strips, membranes, sheets, duracytes, wells and walls of reaction trays, plastic tubes etc. The ligand or agent may be bound to many different carriers. Examples of well-known carriers include glass, polystyrene, polyvinyl chloride, polypropylene, polyethylene, polycarbonate, dextran, nylon, amyloses, natural and modified celluloses, polyacrylamides, agaroses, and magnetite. The nature of the carrier can be either soluble or insoluble for the purposes of the invention. Suitable methods for fixing/immobilizing said ligand are well known and include, but are not limited to ionic, hydrophobic, covalent interactions and the like. It is also contemplated to use "suspension arrays" as arrays according to the present invention (Nolan 2002, Trends Biotechnol. 20(1):9-12). In such suspension arrays, the carrier, e.g. a microbead or microsphere, is present in suspension. The array consists of different microbeads or microspheres, possibly labelled, carrying different ligands. Methods of producing such arrays, for example based on solid-phase chemistry and photo-labile protective groups, are generally known (U.S. Pat. No. 5,744,305).

Measurement of the binding of a ligand, according to preferred embodiments, is performed by an analyzing unit of a system disclosed herein. Thereafter, an amount of the measured binding may be calculated by a computing device of a system disclosed herein.

The term "amount" as used herein encompasses the absolute amount of a polypeptide or peptide, the relative amount or concentration of the said polypeptide or peptide as well as any value or parameter which correlates thereto or can be derived therefrom. Such values or parameters comprise intensity signal values from all specific physical or chemical properties obtained from the said peptides by direct measurements, e.g., intensity values in mass spectra or NMR spectra. Moreover, encompassed are all values or parameters which are obtained by indirect measurements specified elsewhere in this description, e.g., response levels determined from biological read out systems in response to the peptides or intensity signals obtained from specifically bound ligands. It is to be understood that values correlating to the aforementioned amounts or parameters can also be obtained by all standard mathematical operations. According to preferred embodiments of the present invention, the determination of an "amount" is performed by the system of the invention, whereby a computing device determines the "amount" based on contacting and measuring steps performed by one or more analyzing units of said system.

The term "comparing" as used herein encompasses comparing the determined amount for at least one angiogenesis biomarker as referred to herein to a reference. It is to be understood that comparing as used herein refers to any kind of comparison made between the value for the amount with the reference. If an identical or decreased value for the amount in comparison with the reference in the cases of sFlt-1 and Endoglin and an identical or increased value in the case of PlGF is determined, the pregnant subject is not at risk for developing preeclampsia within the short time window ("rule-out" for preeclampsia).

The comparison referred to in step (b) of the method of the present invention may be carried out manually or computer assisted. The value of the amount and the reference can be, e.g., compared to each other and the said comparison can be automatically carried out by a computer program executing an algorithm for the comparison. The computer program carrying out the said evaluation will provide the desired assessment in a suitable output format. Preferably, the evaluation unit of the device of the invention or the computing device of the system of the invention can be used for carrying out the said comparison. The computer program carrying out the said evaluation will provide the desired assessment in a suitable output format. For a computer assisted comparison, the value of the determined amount may be compared to values corresponding to suitable references which are stored in a database by a computer program. The computer program may further evaluate the result of the comparison, i.e. automatically provide the desired assessment in a suitable output format. Based on the comparison of the determined amount and the reference amount, it is possible to make the desired assessment. For example, a result of a comparison may be given as raw data (absolute or relative amounts), and in some cases as an indicator in the form of a word, phrase, symbol, or numerical value which may be indicative of a particular diagnosis.

The term "reference" as used herein refers to a reference amount or value which represents a cut-off for making the diagnosis with a negative predictive value of at least about 98%. Preferably, the negative predictive value envisaged in this context is about 99% or, most preferably, 100%. A suitable cut-off amount or value can be, preferably, determined as discussed above based on sensitivity, specificity and expected, known (e.g., from literature) or estimated (e.g, based on a prospective cohort study) prevalence for preeclampsia in a certain population of subjects to be investigated. A cut-off value or amount to be used as reference can be determined by various techniques known in the art. Preferably, receiver-operating characteristics (ROC) can be used for determining cut-off values or amounts (see especially Zweig 1993, Clin. Chem. 39:561-577). The ROC graph is a plot of all of the sensitivity and specificity pairs resulting from continuously varying the decision threshold (i.e. cut-off value) over the entire range of data observed. The clinical performance of a diagnostic method depends on its accuracy, i.e. its ability to correctly allocate subjects to a certain prognosis or diagnosis. The ROC plot indicates the overlap between the two distributions (results of the affected and the unaffected subgroup) by plotting the sensitivity versus 1-specificity for the complete range of thresholds suitable for making a distinction. On the y-axis is sensitivity, or the true-positive fraction, which is defined as the ratio of number of true-positive test results to the sum of number of true-positive and number of false-negative test results. This has also been referred to as positivity in the presence of a disease or condition. It is calculated solely from the affected subgroup. On the x-axis is the false-positive fraction, or 1-specificity, which is defined as the ratio of number of false-positive results to the sum of number of true-negative and number of false-positive results. It is an index of specificity and is calculated entirely from the unaffected subgroup. Because the true- and false-positive fractions are calculated entirely separately, by using the test results from two different subgroups, the ROC plot is independent of the prevalence of the event in the cohort. Each point on the ROC plot represents a sensitivity and specificity pair corresponding to a particular decision threshold. A test with perfect discrimination (no overlap in the two distributions of results) has an ROC plot that passes through the upper left corner, where the true-positive fraction is 1.0, or 100% (perfect sensitivity), and the false-positive fraction is 0 (perfect specificity). The theoretical plot for a test with no discrimination (identical distributions of results for the two groups) is a 45° diagonal line from the lower left corner to the upper right corner. Most plots fall in between these two extremes. If the ROC plot falls completely below the 45° diagonal, this is easily remedied by reversing the criterion for "positivity" from "greater than" to "less than" or vice versa. Qualitatively, the closer the plot is to the upper left corner, the higher the overall accuracy of the test. A cut-off value can be derived from the ROC curve allowing for the diagnosis or prediction for a given event with a proper balance of sensitivity and specificity, respectively. Accordingly, the reference to be used for the aforementioned method of the present invention, i.e. a cut-off value which allows discriminating between subjects being not at increased risk can be generated, preferably, by establishing a ROC for said cohort as described above and deriving a cut-off value amount therefrom. Dependent on a desired, preselected sensitivity and specificity or corresponding limits of confidence for a diagnostic method, the ROC plot allows deriving suitable cut-off values. It will be understood that sensitivity and specificity are adjusted such that the group of false negatives is minimal in order to exclude a subject for being at increased risk efficiently (i.e. a rule-out) whereas sensitivity and specificity are adjusted such that the group of false positives is minimal in order for a subject to be assessed as being at an increased risk efficiently (i.e. a rule-in). Moreover, the area under the curve (AUC) values can be derived from the ROC plots giving an indication for the cut-off independent, overall performance of the biomarker. Furthermore, each point of the ROC curve represents a sensitivity and specificity pair at a certain cut off value.

The term "about" in the context of the present invention means +/−20%, +/−10%, +/−5%, +/−2% or +/−1% from the indicated parameters or values. This also takes into account usual deviations caused by measurement techniques and the like. The term, however, also includes the indicated parameters or values precisely.

Figure 8:
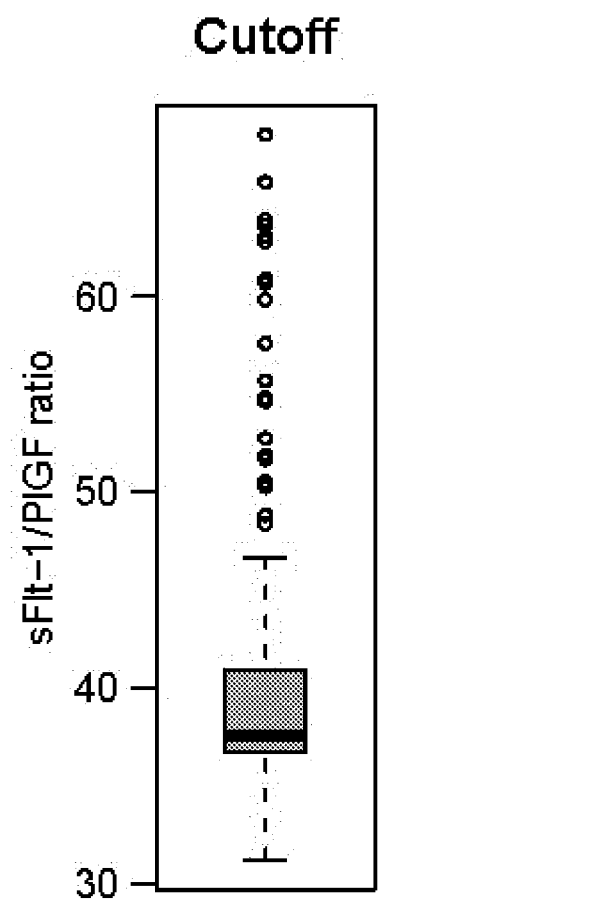
FIG. 8: For the PROGNOSIS study (with 500 patients), the cutoff for the sFlt1-PlGF ratio of preeclampsia within four weeks was determined together with the performance of this cutoff. To avoid overfitting, a cross-validation method, namely a Monte Carlo cross-validation, was applied. For this, all data were splitted into two disjoint subsets—trainingset and testset—with a ratio of 2 to 1. After this split the model was determined on the trainingset and the prediction assessed on the testset. This procedure was repeated 1999 times on randomly chosen trainingset-testset-splits. The consequence were 1999 prediction models with 1999 cutoffs, reflected by the boxplot, with e.g. a median of about 38. This is the same cut off found in the large cohort for ruling out preeclampsia for one week (Example 4).

Advantageously, it has been found in the studies underlying the present invention that the amounts of sFlt-1, Endoglin or PlGF as well as ratios thereof (see also below), i.e. sFlt1/PlGF or Endoglin/PlGF ratio, in a pregnant subject which shows no or limited clinically apparent symptoms of preeclampsia, eclampsia or HELLP syndrome at the time when the samples which are investigated have been taken serve as indicators for a rule out of an imminent preeclampsia, i.e. the development of preeclampsia and/or imminent HELLP syndrome within a short period of about 1 to about 2 weeks. In particular, cut-off amounts or values for the individual biomarkers can be established with a high negative predictive value when using the aforementioned markers. Moreover, ratios of sFLt-1/PlGF of about 46 or even about 33 or less have been found to be particular valuable indicators which allow for a negative predictive value of the method of the present invention of nearly 100%. Also, a ratio of sFLt-1/PlGF of about 38 has been found to be of particular value, as disclosed in detail in the examples, in particular Example 4 and FIG. 8. Accordingly, the method of the present invention operates with a particular high level of confidence with respect to the rule out diagnosis to be established. Moreover, it was found that the method of the present invention could be reliably used not only with samples taken at the first visit of a subject but also with each sample taken at a subsequent visit. Further, the method according to the present invention may be used to identify subjects which have been diagnosed falsely positive to be at risk for developing preeclampsia, eclampsia and/or HELLP syndrome by other diagnostic techniques and, in particular, by uterine Doppler ultrasonography. By applying the method of the present invention to subjects which have been diagnosed by Doppler ultrasonography investigations as being at risk for developing preeclampsia, eclampsia, and/or HELLP syndrome, the subjects for which this diagnosis is falsely positive can be efficiently and reliably ruled out within a short window of time.

Thanks to the present invention, it is possible to more reliably rule out a risk for imminent preeclampsia. Moreover, the time consuming, expensive and cumbersome diagnostic measures such as the current scoring systems or Doppler ultrasonography investigations requiring well trained medical practitioners can be avoided when applying the method of the invention as an aid for diagnosis. In this context, it is of note that in contrast to, e.g., Doppler ultrasonography investigations, the method according to the invention may even be carried out automatically or by medical support staff rather than requiring highly specialized medical practitioners. Health care management shall greatly benefit from the method of the present invention since the need for intensive and special care required, such as close monitoring and also hospitalization, for pregnant females suffering from or being at risk for developing preeclampsia can be better estimated and be taken into account for health care management purposes.

It is to be understood that the definitions and explanations of the terms made above and below apply accordingly for all embodiments described in this specification and the accompanying claims.

In a preferred embodiment of the method of the present invention, said method comprises in step a) determining the amounts of the biomarkers sFlt-1 or Endoglin and PlGF in the sample of said subject and in step c) comparing the value of the ratio of the amounts of the biomarkers sFlt-1 or Endoglin and PlGF in the sample of said subject with a reference value, whereby a subject being not at risk for developing preeclampsia within a short period of time is diagnosed if the value of the ratio is identical or decreased compared to the reference value. More preferably, said method comprises prior to step b) the further step of calculating a ratio from said amounts of sFlt-1 or Endoglin and PlGF determined in the sample in step a).

The term "calculating a ratio" as referred to herein relates to calculating a ratio of the amount of sFlt-1 or Endoglin and the amount of PlGF by dividing the said amounts or by carrying out any other comparable mathematical calculation which puts into a relation the amount of sFlt-1 or Endoglin towards the amount of PlGF. Preferably, the amount of sFlt-1 or Endoglin is divided by the amount of PlGF in order to calculate the ratio, i.e. the ratio is, preferably, amount of sFlt-1 divided by amount of PlGF (also referred to as sFlt-1/PlGF) or amount of Endoglin divided by amount of PlGF (also referred to as Endoglin/PlGF).

The term "comparing" as used herein encompasses comparing the ratio to the reference as defined elsewhere. It is to be understood that comparing as used herein refers to any kind of comparison made between the ratio with the reference. A decreased or not increased risk for developing preeclampsia has been found in the studies underlying the present invention to correlate with a ratio for determined for sFlt-1 or Endoglin and PlGF which is identical or decreased compared to the reference value. More preferably, said reference value for the ratio is about 46, about 45, about 40, or about 35 or less and, preferably, it is about 33 or less. Even more preferably, said reference value for the ratio determined for sFlt-1 and PlGF is about 38 or less; most preferably, said reference value for the ratio determined for sFlt-1 and PlGF is about 38. The aforementioned cut-off values differ considerably compared to those referred to for other (unspecific) rule out approaches for diagnosis on the day of presentation in the prior art (see, e.g., Stepan loc cit.) and achieve a surprisingly high negative predictive value for the prediction when applied in the method of the invention.

In a further preferred embodiment of the method of the present invention, said method further comprises recommending a patient management measure based on the diagnosis.

The term "recommending" as used herein means establishing a proposal for a patient management measure or combinations thereof which could be applied to the subject or which must not be applied to the subject. However, in one particular embodiment, it is to be understood that applying the actual management measure, whatsoever, is not comprised by the term. Patient management measures, as used herein, refer to all measures which can be applied to subjects suffering preeclampsia in order to cure, avoid or handle the said health condition. For example, patient management measures include degree of monitoring (e.g., close, regular or weak monitoring), hospitalization or ambulant maintenance, applying or refraining from drug treatment, or life style recommendations. Preferably, said patient management measure (i) is selected from the group of the following measures if the subject is not diagnosed as being not at risk for developing preeclampsia: close monitoring, hospitalization, administration of blood pressure reducing agents and life style recommendations, and (ii) is ambulant monitoring if the subject is diagnosed as being not at risk for developing preeclampsia.

The present invention further relates to a method of managing a subject suspected to suffer from preeclampsia comprising the steps of the method for diagnosing whether a pregnant subject is not at risk for preeclampsia within a short window of time referred to herein above and the further step of managing the subject according to the established diagnosis. Preferably, said management includes ambulant maintenance of the subject, regular or weak monitoring, refraining from drug administration and, in particular, administration of blood pressure reducing agents or antenatal corticosteroids (e.g. bethamethasone), the latter being applied for accelerating fetal lung maturation in women at risk of preterm birth.

The present invention also relates to the use of at least one of the biomarkers sFlt-1, Endoglin and PlGF or at least one detection agent therefor which specifically bind thereto in a sample of a pregnant subject for diagnosing whether said subject is not at risk for developing preeclampsia within a short period of time. The present invention also includes the use of at least one of the biomarkers sFlt-1, Endoglin and PlGF or at least one detection agent therefor which specifically bind thereto in a sample of a pregnant subject for recommending a patient management measure as set forth elsewhere herein.

Also, the present invention contemplates the use of at least one of the biomarkers sFlt-1, Endoglin and PlGF or at least one detection agent therefor which specifically bind thereto in a sample of a pregnant subject for the manufacture of a diagnostic or pharmaceutical entity or composition for diagnosing whether said subject is not at risk for developing preeclampsia within a short period of time. The present invention also includes the use of at least one of the biomarkers sFlt-1, Endoglin and PlGF or at least one detection agent therefor which specifically bind thereto in a sample of a pregnant subject for the manufacture of a diagnostic or pharmaceutical entity or composition for recommending a patient management measure as set forth elsewhere herein.

The present invention relates to a device adapted for diagnosing whether a pregnant subject is not at risk for developing preeclampsia within a short period of time by carrying out the method of the present invention comprising:
  a) an analyzing unit comprising at least one detection agent which specifically binds to at least one angiogenesis biomarker selected from the group consisting of: sFlt-1, Endoglin and PlGF, said unit being adapted for determining the amount of sFlt-1, Endoglin and/or PlGF in a sample of a pregnant subject; and
  b) an evaluation unit comprising a data processor having implemented an algorithm for comparing the amount with a reference, whereby a subject being not at risk for developing preeclampsia within a short period of time is diagnosed if the amount is identical or decreased compared to the reference in the cases of sFlt-1 and Endoglin and identical or increased in the case of PlGF, wherein said reference allows for making the diagnosis with a negative predictive value of at least about 98%.

The term "device" as used herein relates to a system comprising the aforementioned units operatively linked to each other as to allow the diagnosis according to the methods of the invention. Preferred detection agents which can be used for the analysing unit are disclosed elsewhere herein. The analysing unit, preferably, comprises said detection agents in immobilized form on a solid support which is to be contacted to the sample comprising the biomarkers the amount of which is to be determined. Moreover, the analysing unit can also comprise a detector which determines the amount of detection agent which is specifically bound to the biomarker(s). The determined amount can be transmitted to the evaluation unit. Said evaluation unit comprises a data processing element, such as a computer, with an implemented algorithm for carrying out a calculation of ratios, a comparison of said calculated ratios and an evaluation of the result of the comparison by implementation of an computer-based algorithm carrying out the steps of the method of the present invention set forth elsewhere herein in detail. The results may be given as output of parametric diagnostic raw data. It is to be understood that these data will usually need interpretation by the clinician. However, also envisaged are expert system devices wherein the output comprises processed diagnostic raw data the interpretation of which does not require a specialized clinician.

In a preferred embodiment of the device of the invention, said analysing unit comprises detection agents for determining the amounts of the biomarkers sFlt-1 or Endoglin and PlGF in the sample of said subject and wherein said algorithm implemented in the evaluation unit compares the value of ratio of the amount of sFlt1 or Endoglin and PlGF with a reference value, whereby a subject being not at risk for developing preeclampsia within a short period of time is diagnosed if the value of the ratio is identical or decreased compared to the reference value. Preferably, said algorithm implemented in the evaluation unit further calculates a ratio of the amount of sFlt1 or Endoglin and PlGF.

In another preferred embodiment of the present invention, said evaluation unit further comprises an implemented algorithm which makes a recommendation for a patient management measure based on the diagnosis as set forth elsewhere herein.

It follows from the above that according to some embodiments of the instant disclosure, portions of some steps of methods disclosed and described herein may be performed by a computing device. A computing device may be a general purpose computer or a portable computing device, for example. It should also be understood that multiple computing devices may be used together, such as over a network or other methods of transferring data, for performing one or more steps of the methods disclosed herein. Exemplary computing devices include desktop computers, laptop computers, personal data assistants ("PDA"), such as BLACKBERRY brand devices, cellular devices, tablet computers, servers, and the like. In general, a computing device comprises a processor capable of executing a plurality of instructions (such as a program of software).

A computing device has access to a memory. A memory is a computer readable medium and may comprise a single storage device or multiple storage devices, located either locally with the computing device or accessible to the computing device across a network, for example. Computer-readable media may be any available media that can be accessed by the computing device and includes both volatile and non-volatile media. Further, computer readable-media may be one or both of removable and non-removable media. By way of example, and not limitation, computer-readable media may comprise computer storage media. Exemplary computer storage media includes, but is not limited to, RAM, ROM, EEPROM, flash memory or any other memory technology, CD-ROM, Digital Versatile Disk (DVD) or other optical disk storage, magnetic cassettes, magnetic tape, magnetic disk storage or other magnetic storage devices, or any other medium which can be used for storing a plurality of instructions capable of being accessed by the computing device and executed by the processor of the computing device.

According to embodiments of the instant disclosure, software may include instructions which, when executed by a processor of the computing device, may perform one or more steps of the methods disclosed herein. Some of the instructions may be adapted to produce signals that control operation of other machines and thus may operate through those control signals to transform materials far removed from the computer itself. These descriptions and representations are the means used by those skilled in the art of data processing, for example, to most effectively convey the substance of their work to others skilled in the art.

The plurality of instructions may also comprise an algorithm which is generally conceived to be a self-consistent sequence of steps leading to a desired result. These steps are those requiring physical manipulations of physical quantities. Usually, though not necessarily, these quantities take the form of electrical or magnetic pulses or signals capable of being stored, transferred, transformed, combined, compared, and otherwise manipulated. It proves convenient at times, principally for reasons of common usage, to refer to these signals as values, characters, display data, numbers, or the like as a reference to the physical items or manifestations in which such signals are embodied or expressed. It should be borne in mind, however, that all of these and similar terms are to be associated with the appropriate physical quantities and are merely used here as convenient labels applied to these quantities. According to some embodiments of the instant disclosure, an algorithm for carrying out a comparison between a determined amount of one or more markers disclosed herein, and a suitable reference, is embodied and performed by executing the instructions. The results may be given as output of parametric diagnostic raw data or as absolute or relative amounts. According to various embodiments of the system disclosed herein, a "diagnosis" may be provided by the computing device of a system disclosed herein based on said comparison of the calculated "amount" to a reference or a threshold. For example, a computing device of a system may provide an indicator, in the form of a word, symbol, or numerical value which is indicative of a particular diagnosis.

The computing device may also have access to an output device. Exemplary output devices include fax machines, displays, printers, and files, for example. According to some embodiments of the present disclosure, a computing device may perform one or more steps of a method disclosed herein, and thereafter provide an output, via an output device, relating to a result, indication, ratio or other factor of the method.

The invention further relates to a system for establishing an aid for diagnosing whether a pregnant subject is not at risk for developing preeclampsia within a short period of time by carrying out the method of the present invention comprising:
  a) an analyzing unit configured to bringing the sample into contact with a detection agent (detection agents) that specifically bind(s) to said at least one marker selected from the group consisting of sFlt-1, Endoglin and PlGF for a time sufficient to allow for the formation of a complex of the said detection agent and the at least one marker from the sample, b) an analyzer unit configured to measure the amount of the formed complex, wherein the said amount of the formed complex is proportional to the amount of the at least one marker present in the sample, c) a computing device having a processor and in operable communication with said analysis units, and d) a non-transient machine readable media including a plurality of instructions executable by the processor, the instructions, when executed transform the amount of the formed complex into an amount of the at least one marker reflecting the amount of the at least one marker present in the sample, compare said amount to a reference, and establish an aid for optimizing a risk assessment based on a clinical prediction rule for classifying subjects being at risk for developing preeclampsia within a short period of time based on the result of said comparison to said reference.

A preferred embodiment of the instant disclosure includes a system for optimizing a risk assessment based on a clinical prediction rule for classifying subjects with risk for developing preeclampsia. Examples of systems include clinical chemistry analyzers, coagulation chemistry analyzers, immunochemistry analyzers, urine analyzers, nucleic acid analyzers, used to detect the result of chemical or biological reactions or to monitor the progress of chemical or biological reactions. More specifically, exemplary systems of the instant disclosure may include Roche Elecsys™ Systems and Cobas® e Immunoassay Analyzers, Abbott Architect™ and Axsym™ Analyzers, Siemens Centaur™ and Immulite™ Analyzers, and Beckman Coulter UniCel™ and Acess™ Analyzers, or the like.

Embodiments of the system may include one or more analyzer units utilized for practicing the subject disclosure. The analyzing units of the system disclosed herein are in operable communication with the computing device disclosed herein through any of a wired connection, Bluetooth, LANS, or wireless signal, as are known. Additionally, according to the instant disclosure, an analyzing unit may comprise a stand-alone apparatus, or module within a larger instrument, which performs one or both of the detection, e.g. qualitative and/or quantitative evaluation of samples for diagnostic purpose. For example, an analyzing unit may perform or assist with the pipetting, dosing, mixing of samples and/or reagents. An analyzing unit may comprise a reagent holding unit for holding reagents to perform the assays. Reagents may be arranged for example in the form of containers or cassettes containing individual reagents or group of reagents, placed in appropriate receptacles or positions within a storage compartment or conveyor. Detection reagents may also be in immobilized form on a solid support which are contacted with the sample. Further, an analyzing unit may include a process and/or detection component which is optimizable for specific analysis.

According to some embodiments, an analyzing unit may be configured for optical detection of an analyte, for example a marker, with a sample. An exemplary analyzing unit configured for optical detection comprises a device configured for converting electro-magnetic energy into an electrical signal, which includes both single and multi-element or array optical detectors. According to the present disclosure, an optical detector is capable of monitoring an optical electro-magnetic signal and providing an electrical outlet signal or response signal relative to a baseline signal indicative of the presence and/or concentration of an analyte in a sample being located in an optical path. Such devices may also include, for example, photodiodes, including avalanche photodiodes, phototransistors, photoconductive detectors, CCD detectors, CMOS detectors, linear sensor arrays, CCD detectors, CMOS detectors, including CMOS array detectors, photomultipliers, and photomultiplier arrays. According to certain embodiments, an optical detector, such as a photodiode or photomultiplier, may contain additional signal conditioning or processing electronics. For example, an optical detector may include at least one pre-amplifier, electronic filter, or integrated circuit. Suitable pre-preamplifiers include, for example, integrating, transimpedance, and current gain (current mirror) pre-amplifiers.

Additionally, one or more analyzing unit according to the instant disclosure may comprise a light source for emitting light. For example, a light source of an analyzing unit may consist of at least one light emitting element (such as a light emitting diode, an electric powered radiation source such as an incandescent lamp, an electroluminescent lamp, a gas discharge lamp, a high-intensity discharge lamp, a laser) for measuring analyte concentrations with a sample being tested or for enabling an energy transfer (for example, through florescent resonance energy transfer or catalyzing an enzyme).

Further, an analyzing unit of the system may include one or more incubation units (for example, for maintaining a sample or a reagent at a specified temperature or temperature range). In some embodiments, an analyzer unit may include a thermocycler, include a real-time thermocycler, for subjecting a sample to repeated temperature cycles and monitoring a change in the amount of an amplification product with the sample.

Additionally, an analyzing unit of the system disclosed herein may comprise, or be operationally connected to, a reaction vessel or cuvette feeding unit. Exemplary feeding units include liquid processing units, such as a pipetting unit, to deliver samples and/or reagents to the reaction vessels. The pipetting unit may comprise a reusable washable needle, e.g. a steel needle, or disposable pipette tips. The analyzing unit may further comprise one or more mixing units, for example a shaker to shake a cuvette comprising a liquid, or a mixing paddle to mix liquids in a cuvette, or reagent container.

The present invention also relates to a kit adapted for carrying out the method of the present invention comprising at least one detection agent for determining the amount of an angiogenesis biomarker selected from the group consisting of: sFlt-1, Endoglin and PlGF, as well as instructions for carrying out the said method.

The term "kit" as used herein refers to a collection of the aforementioned components, preferably, provided in separately or within a single container. The container also comprises instructions for carrying out the method of the present invention. These instructions may be in the form of a manual or may be provided by a computer program code which is capable of carrying out the calculations and comparisons referred to in the methods of the present invention and to establish a diagnosis accordingly when implemented on a computer or a data processing device. The computer program code may be provided on a data storage medium or device such as a optical storage medium (e.g., a Compact Disc) or directly on a computer or data processing device. Moreover, the kit may, preferably, comprise standard amounts for the biomarkers as described elsewhere herein for calibration purposes.

In a preferred embodiment of the kit of the invention, said kit comprises a detection agent for determining the amount of sFlt1 and/or Endoglin and a detection agent for determining the amount of PlGF in a sample of a pregnant subject.

In some embodiments, a kit disclosed herein includes at least one component or a packaged combination of components for practicing a disclosed method. By "packaged combination" it is meant that the kits provide a single package that contains a combination of one or more components, such as probes (for example, an antibody), controls, buffers, reagents (for example, conjugate and/or substrate) instructions, and the like, as disclosed herein. A kit containing a single container is also included within the definition of "packaged combination." In some embodiments, the kits include at least one probe, for example an antibody (having specific affinity for an epitope of a biomarker as disclosed herein. For example, the kits may include an antibody that is labelled with a fluorophore or an antibody that is a member of a fusion protein. In the kit, the probe may be immobilized, and may be immobilised in a specific conformation. For example, an immobilized probe may be provided in a kit to specifically bind target protein, to detect target protein in a sample, and/or to remove target protein from a sample.

According to some embodiments, kits include at least one probe, which may be immobilized, in at least one container. Kits may also include multiple probes, optionally immobilized, in one or more containers. For example, the multiple probes may be present in a single container or in separate containers, for example, wherein each container contains a single probe.

In some embodiments, a kit may include one or more non-immobilized probe and one or more solid support that does or does not include an immobilized probe. Some such embodiments may comprise some or all of the reagents and supplies needed for immobilizing one or more probes to the solid support, or some or all of the reagents and supplies needed for binding of immobilized probes to specific proteins within a sample.

In certain embodiments, a single probe (including multiple copies of the same probe) may be immobilized on a single solid support and provided in a single container. In other embodiments, two or more probes, each specific for a different target protein or a different form of a single target protein (such as a specific epitope), a provided in a single container. In some such embodiments, an immobilized probe may be provided in multiple different containers (e.g., in single-use form), or multiple immobilized probes may be provided in multiple different containers. In further embodiments, the probes may be immobilized on multiple different type of solid supports. Any combination of immobilized probe(s) and container(s) is contemplated for the kits disclosed herein, and any combination thereof may be selected to achieve a suitable kit for a desired use.

A container of the kits may be any container that is suitable for packaging and/or containing one or more components disclosed herein, including for example probes (for example, an antibody), controls, buffers, and reagents (for example, conjugate and/or substrate). Suitable materials include, but are not limited to, glass, plastic, cardboard or other paper product, wood, metal, and any alloy thereof. In some embodiments, the container may completely encase an immobilized probe(s) or may simply cover the probe to minimize contamination by dust, oils, etc., and expose to light. In some further embodiments, the kits may comprise a single container or multiple containers, and where multiple containers are present, each container may be the same as all other containers, different than others, or different than some but not all other containers.

In an aspect of the invention, a method for establishing an aid for ruling out preeclampsia within a short window of time is contemplated, said method comprising:

a) determining the amount of at least one angiogenesis biomarker referred to herein in a sample of a pregnant subject, said determining comprises (i) bringing the sample into contact with a detection agent that specifically binds to said at least one angiogenesis biomarker for a time sufficient to allow for the formation of a complex of the said detection agent and the biomarker from the sample, (ii) measuring the amount of the formed complex, wherein the said amount of the formed complex is proportional to the amount of the at least one biomarker present in the sample, and (iii) transforming the amount of the formed complex into an amount of the at least one biomarker reflecting the amount of the at least one biomarker present in the sample;

b) comparing said amount to a reference; and c) establishing an aid for ruling out preeclampsia within a short window of time based on the result of the comparison made in step b).

A suitable detection agent may be, in an aspect, an antibody which specifically binds to at least one angiogenesis biomarker in a sample of a subject to be investigated by the method of the invention. Another detection agent that can be applied, in an aspect, may be an aptamere which specifically binds to at least one angiogenesis biomarker in the sample. In yet an aspect, the sample is removed from the complex formed between the detection agent and the at least one angiogenesis biomarker prior to the measurement of the amount of formed complex. Accordingly, in an aspect, the detection agent may be immobilized on a solid support. In yet an aspect, the sample can be removed from the formed complex on the solid support by applying a washing solution. The formed complex shall be proportional to the amount of the at least one angiogenesis biomarker present in the sample. It will be understood that the specificity and/or sensitivity of the detection agent to be applied defines the degree of proportion of at least one angiogenesis biomarker comprised in the sample which is capable of being specifically bound. Further details on how the determination can be carried out are also found elsewhere herein. The amount of formed complex shall be transformed into an amount of at least one angiogenesis biomarker reflecting the amount indeed present in the sample. Such an amount, in an aspect, may be essentially the amount present in the sample or may be, in another aspect, an amount which is a certain proportion thereof due to the relationship between the formed complex and the amount present in the original sample.

In yet an aspect of the aforementioned method, step a) may be carried out by an analyzing unit, in an aspect, an analyzing unit as defined elsewhere herein. In other aspects, any or all of steps a) through c) may be carried out by an analyzing unit as defined elsewhere herein. In an aspect of the method of the invention, the amount determined in step a) is compared to a reference. In an aspect, the reference is a reference as defined elsewhere herein. In yet another aspect, the reference takes into account the proportional relationship between the measured amount of complex and the amount present in the original sample. Thus, the references applied in an aspect of the method of the invention are artificial references which are adopted to reflect the limitations of the detection agent that has been used. In another aspect, said relationship can be also taken into account when carrying out the comparison, e.g., by including a normalization and/or correction calculation step for the determined amount prior to actually comparing the value of the determined amount and the reference. Again, the normalization and/or correction calculation step for the determined amount adopts the comparison step such that the limitations of the detection agent that has been used are reflected properly. In an aspect, the comparison is carried out automatically, e.g., assisted by a computer system or the like.

The aid for diagnosing is established based on the comparison carried out in step b) by unambiguously allocating the subject into the group of subjects which are not at risk of developing preeclampsia within a short window of time or ambiguously excluding it from said group. As discussed elsewhere herein already, the allocation of the investigated subject must not be correct in 100% of the investigated cases. The groups of subjects into which the investigated subject is allocated are artificial groups in that they are established based on statistical considerations, i.e. a certain preselected degree of likelihood based on which the method of the invention shall operate. Thus, the method may establish an aid of diagnosis which may, in an aspect, require further strengthening of the diagnosis by other techniques. In an aspect of the invention, the aid for diagnosing is established automatically, e.g., assisted by a computer system or the like.

In an aspect of the method of the invention, said method further comprises a step of treating/prescribing/recommending or managing the subject according to the result of the aid of diagnosis established in step c) as set for the elsewhere herein.

In an aspect of the aforementioned method, steps b) and/or c) are carried out by an evaluation unit as set forth elsewhere herein.

All references cited in this specification are herewith incorporated by reference with respect to their entire disclosure content and the disclosure content specifically mentioned in this specification.

EXAMPLES

The following Examples shall merely illustrate the invention. They shall not be construed, whatsoever, to limit the scope of the invention.

Example 1

Determination of Blood Levels of sFlt-1, Endoglin and PlGF

Blood levels of sFlt-1, PlGF and Endoglin were determined using the commercially available immunoassays. In particular the following assays have been used.

sFlt-1 was determined with sandwich immunoassays using analysers from the Roche Elecsys™- or Cobas E™-series. The assay comprises two monoclonal antibodies specific for the respective polypeptide. The first of these antibodies is biotinylated and the second one is labelled with a Tris(2,2'-bipyridyl)ruthenium(II)-complex. In a first incubation step both antibodies are incubated with the sample. A sandwich complex comprising the peptide to be determined and the two different antibodies is formed. In a next incubation step streptavidin-coated beads are added to this complex. The beads bind to the sandwich complexes. The reaction mixture is then aspirated into a measuring cell where the beads are magnetically captured on the surface of an electrode. The application of a voltage then induces a chemiluminescent emission from the ruthenium complex which is measured by a photomultiplier. The emitted amount of light is dependent on the amount of sandwich complexes on the electrode. The sFlt-1 test is commercially available from Roche Diagnostics GmbH, Mannheim, Germany. Further details on the assay are found in the package insert. The measuring range of sFlt-1 includes amounts between 10 to 85,000 pg/ml.

Endoglin was measured using the Quantikine™ Human Endoglin/CD 105 immunoassay which is commercially available from R&D Systems, Inc, Minneapolis, US. This assay employs the quantitative sandwich enzyme immunoassay technique. A monoclonal antibody specific for Endoglin has been pre-coated onto a microplate. Standards and samples are pipetted into the wells and any Endoglin present is bound by the immobilized antibody. After washing away any unbound substances, an enzyme-linked monoclonal antibody specific for Endoglin is added to the wells. Following a wash to remove any unbound antibody-enzyme reagent, a substrate solution is added to the wells and color develops in proportion to the amount of Endoglin bound in the initial step. The color development is stopped and the intensity of the color is measured. Further details on the assay are found in the package insert. The measuring range of Endoglin includes amounts between 0.001 ng/L to 10 ng/ml.

PlGF was tested using two PlGF specific antibodies in a sandwich immunoassay which is carried out on an Elecsys™- or Cobas E™-series analyser (see above for details). The PlGF test is commercially available from Roche Diagnostics GmbH, Mannheim, Germany. Further details on the assay are found in the package insert. The measuring range of PlGF includes amounts of 3 to 10,000 pg/ml.

Example 2

Analysis of Preeclampsia as Outcome within 1 Week

In the tables which were used to produce the ROC curve, one can select cut-off values with the target NPV and estimate sensitivity, specificity, and PPV at this cut-off. For all these proportions confidence intervals are available based on the current sample size.

For patients between week 24+/−0 and week 40+/−0 after gestation, a cut off of 45 for the sFlt-1/PlGF ratio determined in a sample obtained at the first visit yielded a NPV of 100% (lower 95% confidence limit 96.58%) to predict preeclampsia, with a sensitivity estimate of 100% (LCL95 66.37%) and a specificity estimate of 80.92% (LCL95 73.13%). The PPV estimate is 26.47% (LCL95 12.88%). 34 vs. 106 subjects were test positive/negative at this cut off, 9 out of the 34 are expected to develop PE, but none of the 106.

For patients between week 24+/−0 and week 40+/−0 after gestation, a cut off of 45 for the sFlt-1/PlGF ratio determined in samples obtained at multiple visits yielded a npv of 99.43% (lower 95% confidence limit 97.96%) is estimated, with a sensitivity estimate of 86.67% (LCL95 63.66%) and a specificity estimate of 80.60% (LCL95 76.56%). The PPV estimate is 13.40% (LCL95 7.33%). At 97 vs. 351 visits subjects were tested positive/negative at this cut off, 13 out of the 94 visits preceded a PE, but 2 of the 351.

The results are also summarized in the following table:

TABLE 1

AUC, LCL95 and UCL95 values

| response | biomarker | auc | LCL95 | ucl95 |
|---|---|---|---|---|
| PE within 1 week | ratio_sFlt_1_PlGF | 0.9211 | 0.8703 | 0.9719 |
| PE within 1 week | ratio_endogl_PlGF | 0.9118 | 0.8448 | 0.9788 |
| PE within 1 week | tst_res_sFlt_1_pg_ml | 0.933 | 0.8889 | 0.9771 |
| PE within 1 week | tst_res_PlGF_pg_ml | 0.8482 | 0.7608 | 0.9356 |
| PE within 1 week | endogl_ng_ml | 0.9254 | 0.8615 | 0.9892 |
| PE within 1 week-all visits | ratio_sFlt_1_PlGF | 0.9108 | 0.8689 | 0.9528 |
| PE within 1 week-all visits | ratio_endogl_PlGF | 0.8949 | 0.8493 | 0.9405 |
| PE within 1 week-all visits | tst_res_sFlt_1_pg_ml | 0.9087 | 0.849 | 0.9684 |
| PE within 1 week-all visits | tst_res_PlGF_pg_ml | 0.8618 | 0.8112 | 0.9124 |
| PE within 1 week-all visits | endogl_ng_ml | 0.8928 | 0.8419 | 0.9437 |
| PE within 2 weeks | ratio_sFlt_1_PlGF | 0.9262 | 0.8788 | 0.9735 |
| PE within 2 weeks | ratio_endogl_PlGF | 0.9108 | 0.8487 | 0.9729 |
| PE within 2 weeks | tst_res_sFlt_1_pg_ml | 0.9438 | 0.9041 | 0.9836 |
| PE within 2 weeks | tst_res_PlGF_pg_ml | 0.8485 | 0.7681 | 0.9288 |
| PE within 2 weeks | endogl_ng_ml | 0.9238 | 0.865 | 0.9827 |
| PE within 2 weeks-all visits | ratio_sFlt_1_PlGF | 0.8978 | 0.8566 | 0.939 |
| PE within 2 weeks-all visits | ratio_endogl_PlGF | 0.873 | 0.8305 | 0.9155 |
| PE within 2 weeks-all visits | tst_res_sFlt_1_pg_ml | 0.8897 | 0.8356 | 0.9437 |
| PE within 2 weeks-all visits | tst_res_PlGF_pg_ml | 0.8568 | 0.8116 | 0.9021 |
| PE within 2 weeks-all visits | endogl_ng_ml | 0.8615 | 0.8161 | 0.9069 |
| PE within 4 weeks | ratio_sFlt_1_PlGF | 0.89 | 0.8355 | 0.9445 |
| PE within 4 weeks | ratio_endogl_PlGF | 0.8608 | 0.7977 | 0.9239 |
| PE within 4 weeks | tst_res_sFlt_1_pg_ml | 0.9034 | 0.8447 | 0.9621 |
| PE within 4 weeks | tst_res_PlGF_pg_ml | 0.8331 | 0.7663 | 0.8999 |
| PE within 4 weeks | endogl_ng_ml | 0.8651 | 0.801 | 0.9293 |
| PE within 4 weeks-all visits | ratio_sFlt_1_PlGF | 0.8655 | 0.8261 | 0.9049 |
| PE within 4 weeks-all visits | ratio_endogl_PlGF | 0.8369 | 0.797 | 0.8768 |
| PE within 4 weeks-all visits | tst_res_sFlt_1_pg_ml | 0.861 | 0.8168 | 0.9053 |
| PE within 4 weeks-all visits | tst_res_PlGF_pg_ml | 0.8262 | 0.7806 | 0.8717 |
| PE within 4 weeks-all visits | endogl_ng_ml | 0.8233 | 0.7801 | 0.8666 |

Example 3

Comparison of the Diagnostic Performance of Biomarker Ratios sFlt-1/PlG and Endoglin/PlGF to Doppler Ultrasonography Results in Pregnant Women for Prediction of PE/HELLP within a Short Window of Time Comparison of mPI-UtA, sFlt-1/PlGF ratio and Endoglin/PlGF ratio as classifiers (using cutoff values) if a patient develops PE/HELLP syndrome within one/four weeks after the visit. Population here are pregnant women with available Doppler sonography result:

TABLE 2

Comparison of mPI-UtA, sFlt-1/PlGF ratio and Endoglin/PlGF ratio as classifiers

| Endpoint | Positive result if: | Proportion | [%] | 95% CI | Abs. [N] |
|---|---|---|---|---|---|
| Diagnosis of PE/HELLP within one week after visit | mPI-UtA > 95. Percentile | Sensitivity | 75.0 | 19.4-99.4 | 3/4 |
| | | Specificity | 53.3 | 42.5-63.9 | 48/90 |
| | sFlt-1/PlGF ratio ≥ 46 | Sensitivity | 100.0 | 39.8-100.0 | 4/4 |
| | | Specificity | 80.0 | 70.2-87.7 | 72/90 |
| | Endoglin/PlGF ratio ≥ 0.2 | Sensitivity | 75.0 | 19.4-99.4 | 3/4 |
| | | Specificity | 76.7 | 66.6-84.9 | 69/90 |
| Diagnosis of PE/HELLP within four weeks after visit | mPI-UtA > 95. Percentile | Sensitivity | 55.6 | 21.2-86.3 | 5/9 |
| | | Specificity | 51.9 | 40.4-63.3 | 41/79 |
| | sFlt-1/PlGF ratio ≥ 46 | Sensitivity | 77.8 | 40.0-97.2 | 7/9 |
| | | Specificity | 82.3 | 72.1-90.0 | 65/79 |
| | Endoglin/PlGF ratio ≥ 0.2 | Sensitivity | 55.6 | 21.2-86.3 | 5/9 |
| | | Specificity | 78.5 | 67.8-86.9 | 62/79 |

Both ratios seem to be superior for both prediction tasks to the Doppler sonography. The sFlt-1/PlGF ratio seem to perform better (with the chosen cutoffs) than the Endoglin/PlGF ratio.

sFlt-1/PlGF ratio and Endoglin/PlGF ratio as classifiers (using cutoff values) if a patient develops PE within one/four weeks after the visit. Population here are all pregnant women with an abnormal Doppler sonography result:

TABLE 3 sFlt-1/PlGF ratio and Endoglin/PlGF ratio as classifiers

| Endpoint | Positive result if: | Proportion | [%] | 95% CI | Abs. [N] |
|---|---|---|---|---|---|
| Diagnosis of PE/HELLP within one week after visit | sFlt-1/PlGF ratio ≥ 46 | Sensitivity | 100.0 | 29.2-100.0 | 3/3 |
| | | Specificity | 81.0 | 65.9-91.4 | 34/42 |
| | Endoglin/PlGF ratio ≥ 0.2 | Sensitivity | 100.0 | 29.2-100.0 | 3/3 |
| | | Specificity | 76.2 | 60.5-87.9 | 32/42 |

TABLE 3-continued

| | sFlt-1/PlGF ratio and Endoglin/PlGF ratio as classifiers | | | | |
|---|---|---|---|---|---|
| Endpoint | Positive result if: | Proportion | [%] | 95% CI | Abs. [N] |
| Diagnosis of PE/HELLP within four weeks after visit | sFlt-1/PlGF ratio ≥ 46 | Sensitivity | 80.0 | 28.4-99.5 | 4/5 |
| | | Specificity | 81.6 | 65.7-92.3 | 31/38 |
| | Endoglin/PlGF ratio ≥ 0.2 | Sensitivity | 60.0 | 14.7-94.7 | 3/5 |
| | | Specificity | 76.3 | 59.8-88.6 | 29/38 |

The sFlt-1/PlGF ratio seems to be superior to the Endoglin/PlGF ratio especially on the four week prediction task.

TABLE 4

Figure 4A:
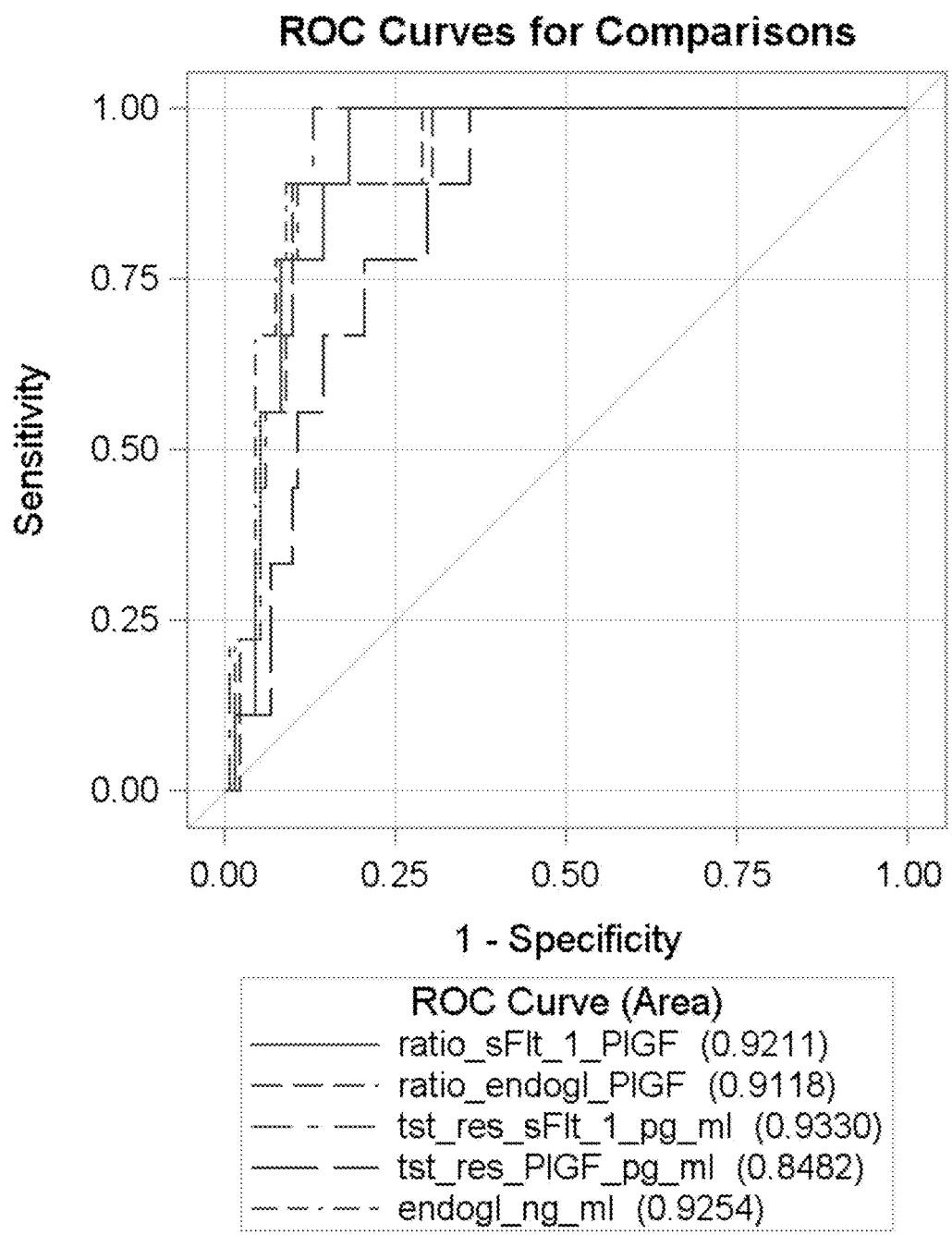
FIG. 4A shows a ROC curve and statistical analysis thereof for no onset of preeclampsia (PE) within 1 week after the sample has been taken (visit). An AUC (area under the curve) of 1.0 qualifies a perfect diagnostic test, an AUC of 0.5 a useless one. The confidence interval for the AUC reflects the precision of the estimate based on the present data; n=94.
Figure 4B:
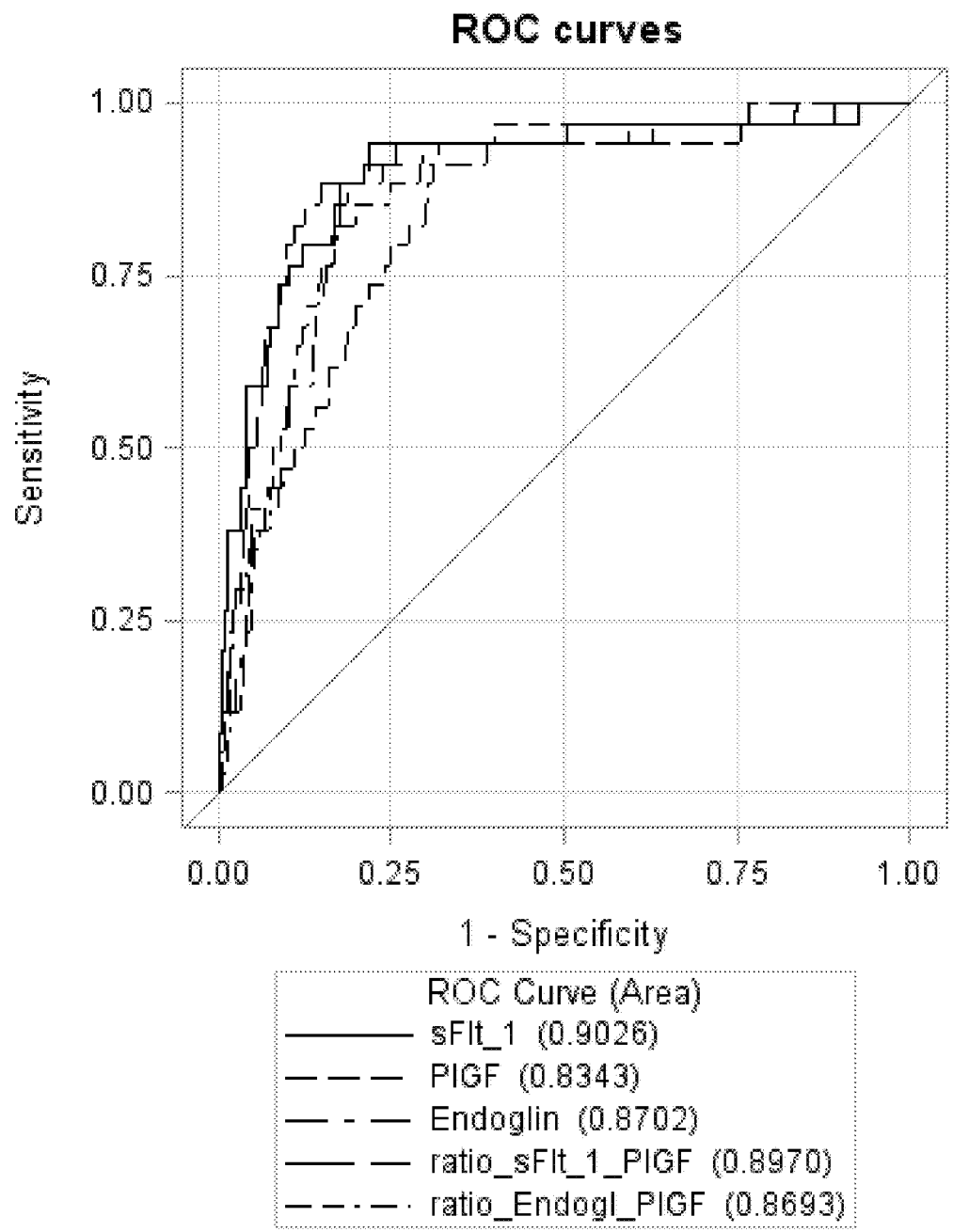
FIG. 4B shows a ROC curve and statistical analysis thereof for no onset of preeclampsia (PE) within 1 week after the sample has been taken (visit). An AUC (area under the curve) of 1.0 qualifies a perfect diagnostic test, an AUC of 0.5 a useless one. The confidence interval for the AUC reflects the precision of the estimate based on the present data; (B) is the same as in (A), but n=269.

ROC association statistics for the values displayed in FIG. 4A
ROC Association Statistics

| | | | Mann-Whitney | | | |
|---|---|---|---|---|---|---|
| ROC Model | Area | Standard Error | 95% Wald Confidence Limits | | Somers' D (Gini) | Gamma | Tau-a |
| ratio_sFlt_1_PlGF | 0.9211 | 0.0259 | 0.8703 | 0.9719 | 0.8422 | 0.8422 | 0.1021 |
| ratio_endogl_PlGF | 0.9118 | 0.0342 | 0.8448 | 0.9788 | 0.8236 | 0.8236 | 0.0998 |
| tst_res_sFlt_1_pg_ml | 0.9330 | 0.0225 | 0.8889 | 0.9771 | 0.8660 | 0.8660 | 0.1049 |
| tst_res_PlGF_pg_ml | 0.8482 | 0.0446 | 0.7608 | 0.9356 | 0.6964 | 0.6964 | 0.0844 |
| endogl_ng_ml | 0.9254 | 0.0326 | 0.8615 | 0.9892 | 0.8507 | 0.8507 | 0.1031 |

TABLE 5

Figure 5A:
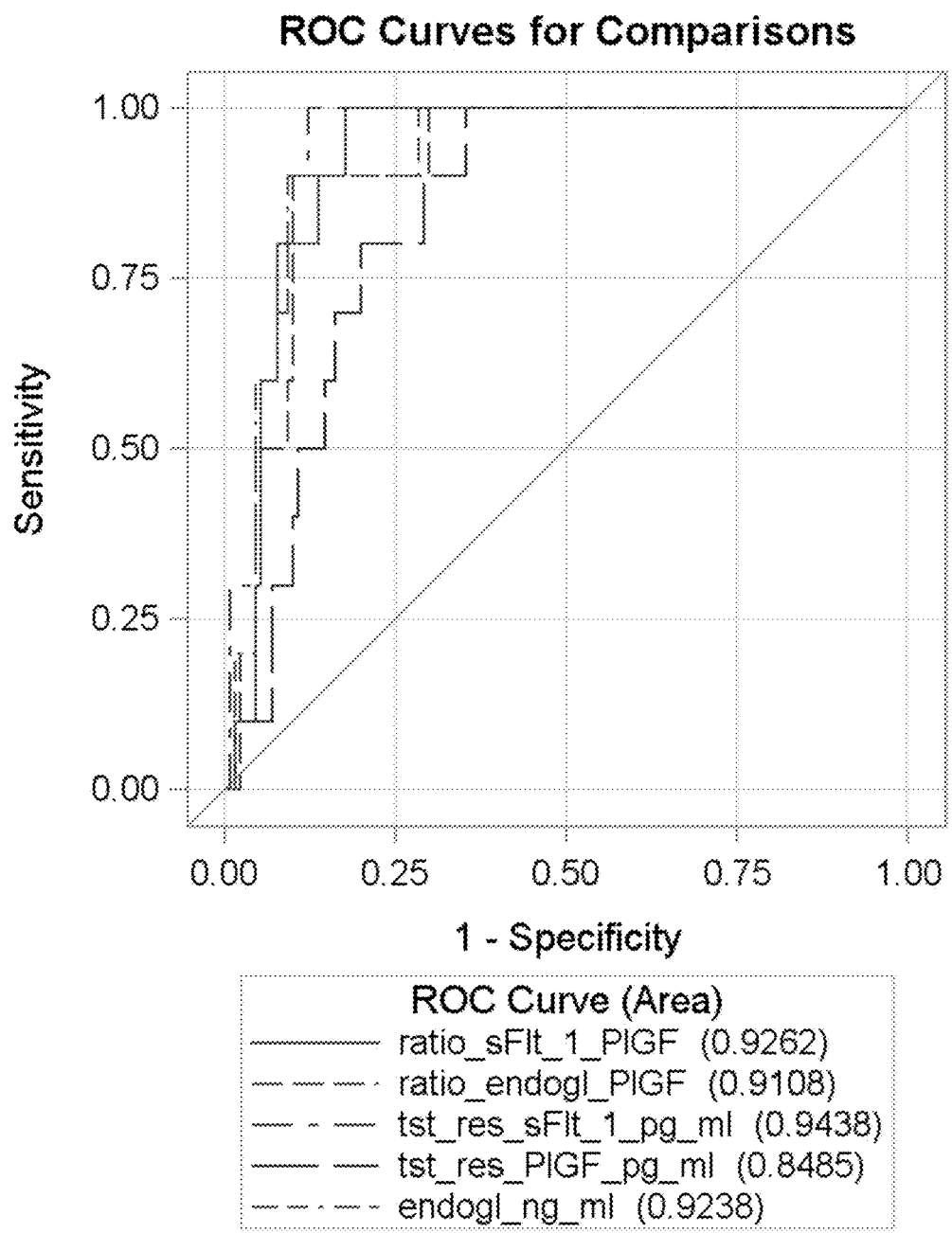
FIG. 5A shows a ROC curve and statistical analysis thereof for no onset of preeclampsia (PE) within 2 weeks after the sample has been taken (visit). An AUC (area under the curve) of 1.0 qualifies a perfect diagnostic test, an AUC of 0.5 a useless one. The confidence interval for the AUC reflects the precision of the estimate based on the present data.
Figure 5B:
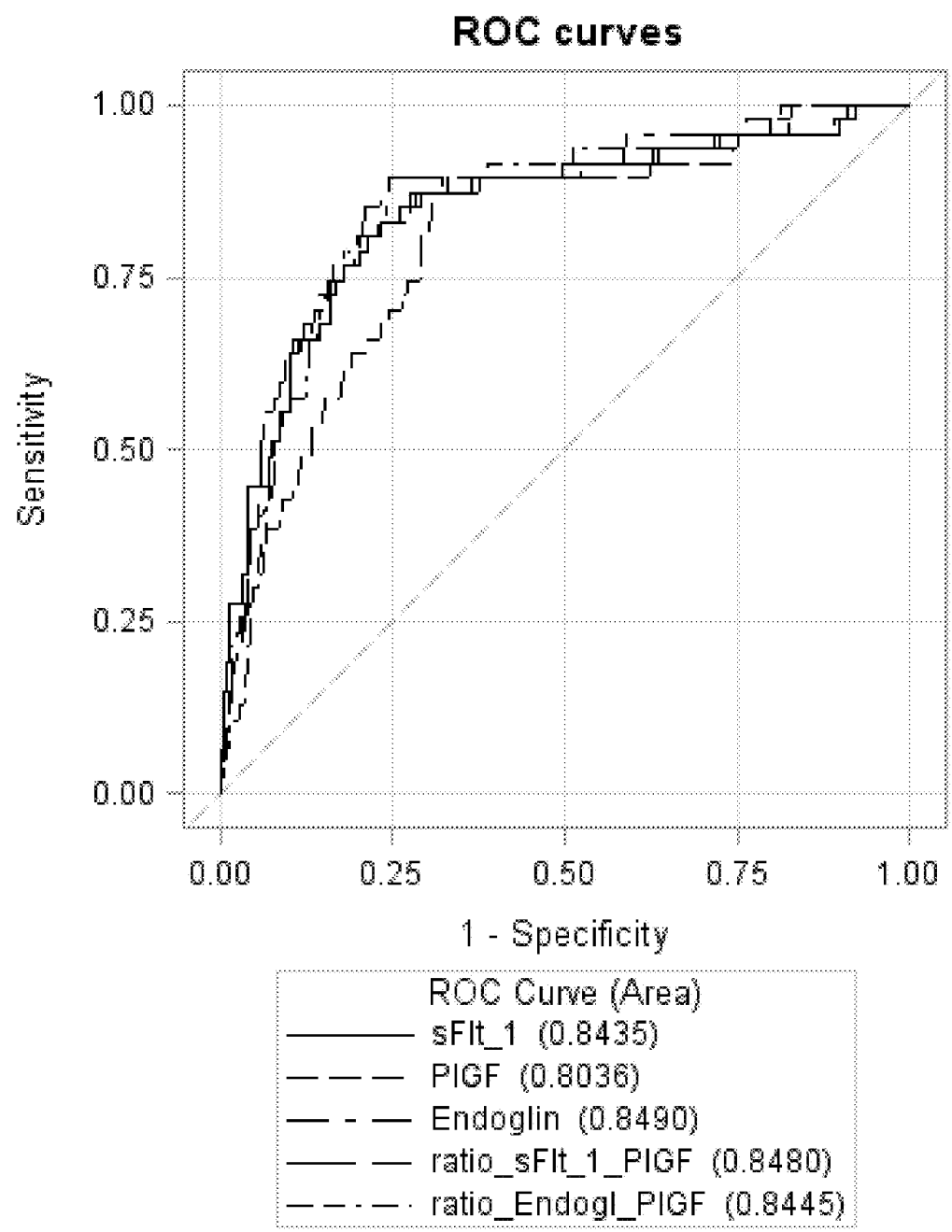
FIG. 5B shows a ROC curve and statistical analysis thereof for no onset of preeclampsia (PE) within 2 weeks after the sample has been taken (visit). An AUC (area under the curve) of 1.0 qualifies a perfect diagnostic test, an AUC of 0.5 a useless one. The confidence interval for the AUC reflects the precision of the estimate based on the present data; (B) is the same as in (A), but n=269.
Figure 6A:
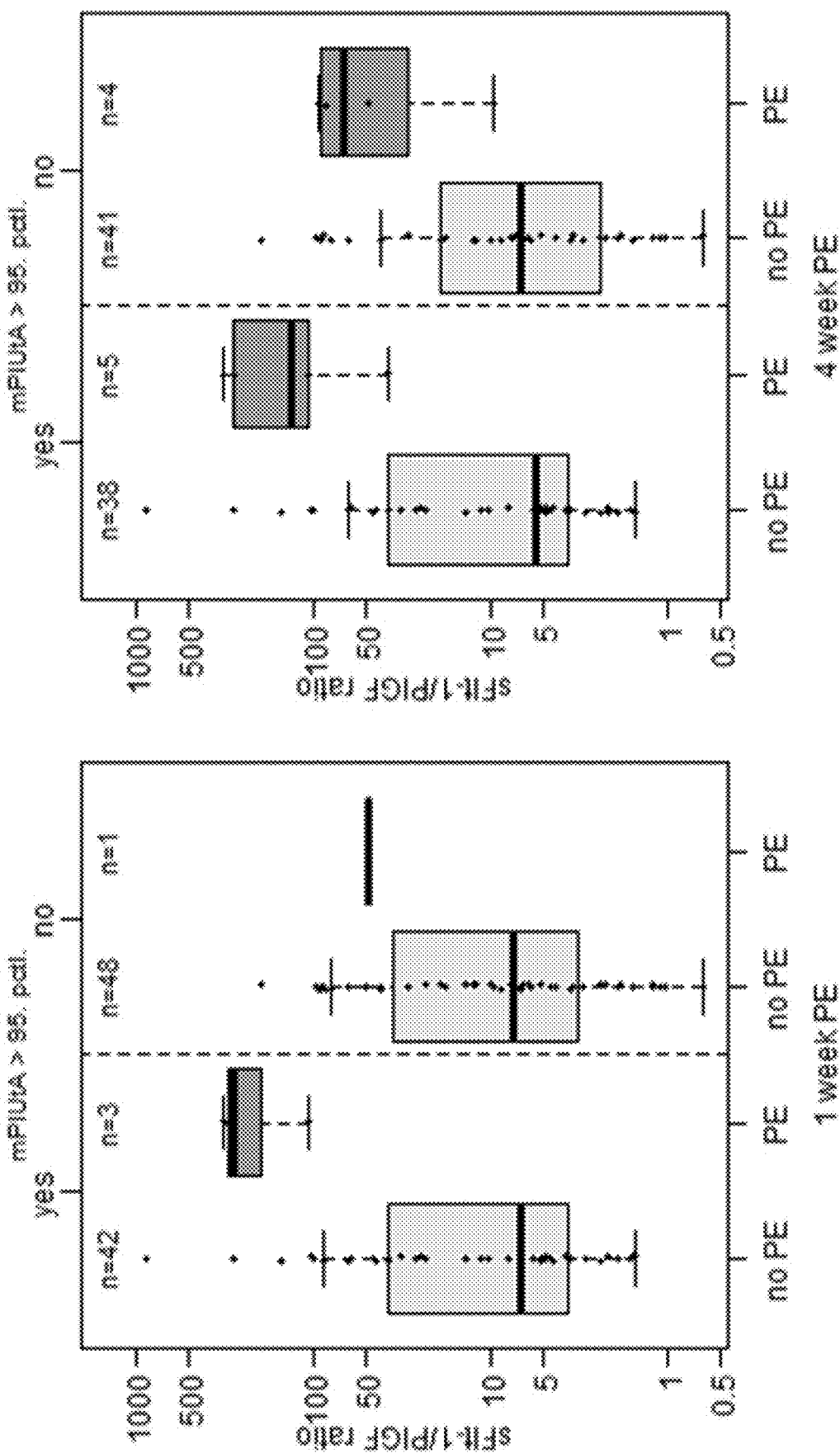
FIG. 6A shows box plot graphs using sFlt-1/PlGF ratio; n=94 for 1 week PE, n=88 for 4 week PE. The left hand side of each graph shows measurements from patients with abnormal Doppler sonography results (mPI-UtA>95. percentile), the right hand side shows measurements from patients with normal results. In addition, measurements are separated for patients that develop PE/HELLP (red boxes) or not (green boxes) within one week (left graph) and four weeks (right graph), respectively. The graphs show that the sFlt-1/PlGF ratio has potential to predict whether a patient will develop a PE or not both within one week and within four weeks, especially in patients with abnormal Doppler sonography results.
Figure 6B:
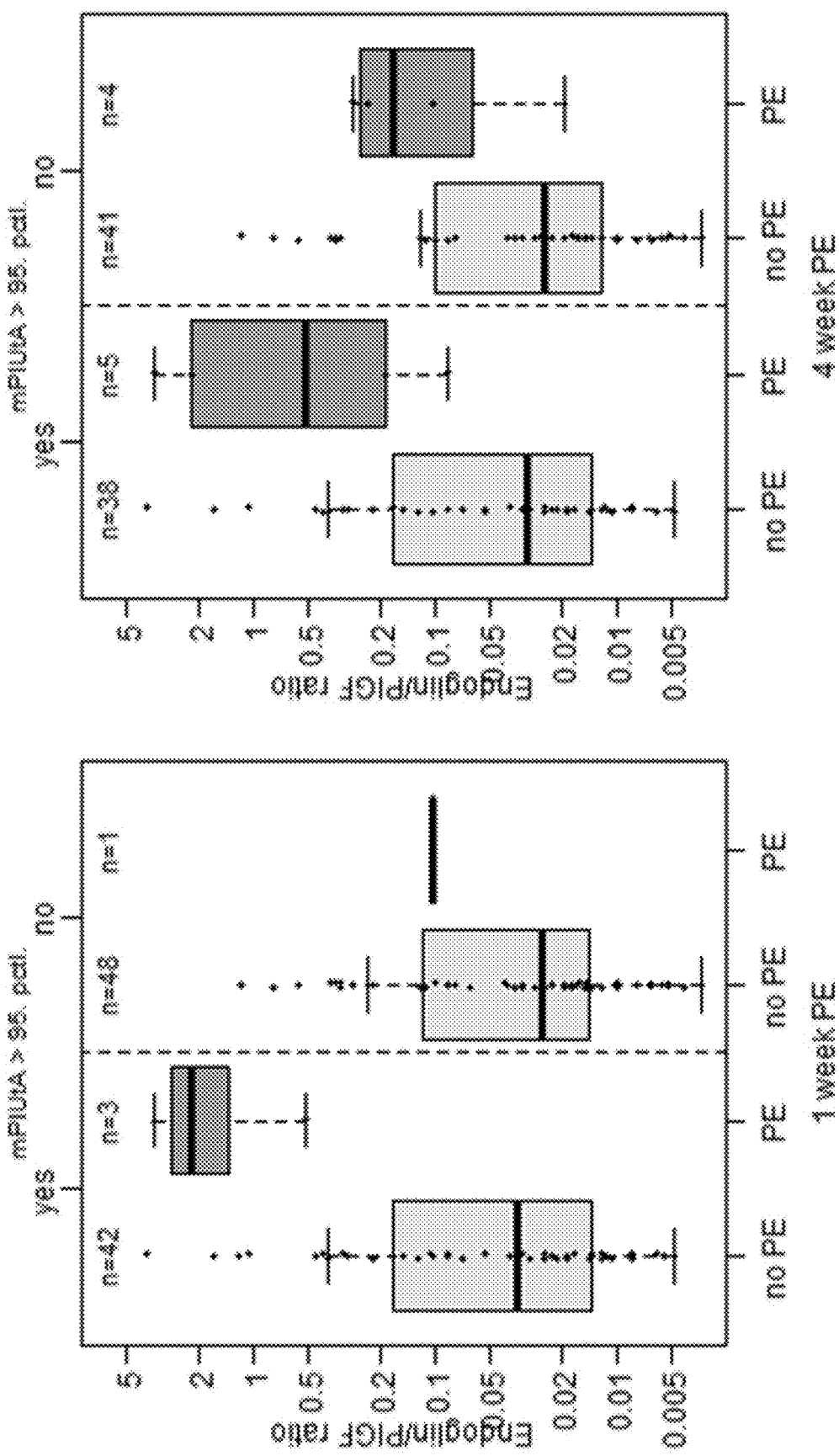
FIG. 6B shows box plot graphs using Endoglin/PlGF ratio; n=94 for 1 week PE, n=88 for 4 week PE. The left hand side of each graph shows measurements from patients with abnormal Doppler sonography results (mPI-UtA>95. percentile), the right hand side shows measurements from patients with normal results. In addition, measurements are separated for patients that develop PE/HELLP (red boxes) or not (green boxes) within one week (left graph) and four weeks (right graph), respectively. The graphs show that the Endoglin/PlGF ratio has potential to predict whether a patient will develop a PE or not both within one week and within four weeks, especially in patients with abnormal Doppler sonography results. The sFlt-1/PlGF ratio seems to distinguish more precisely than the Endoglin/PlGF ratio especially for the prediction of PE/HELLP within four weeks (compare FIG. 6A with FIG. 6B).
Figure 7A:
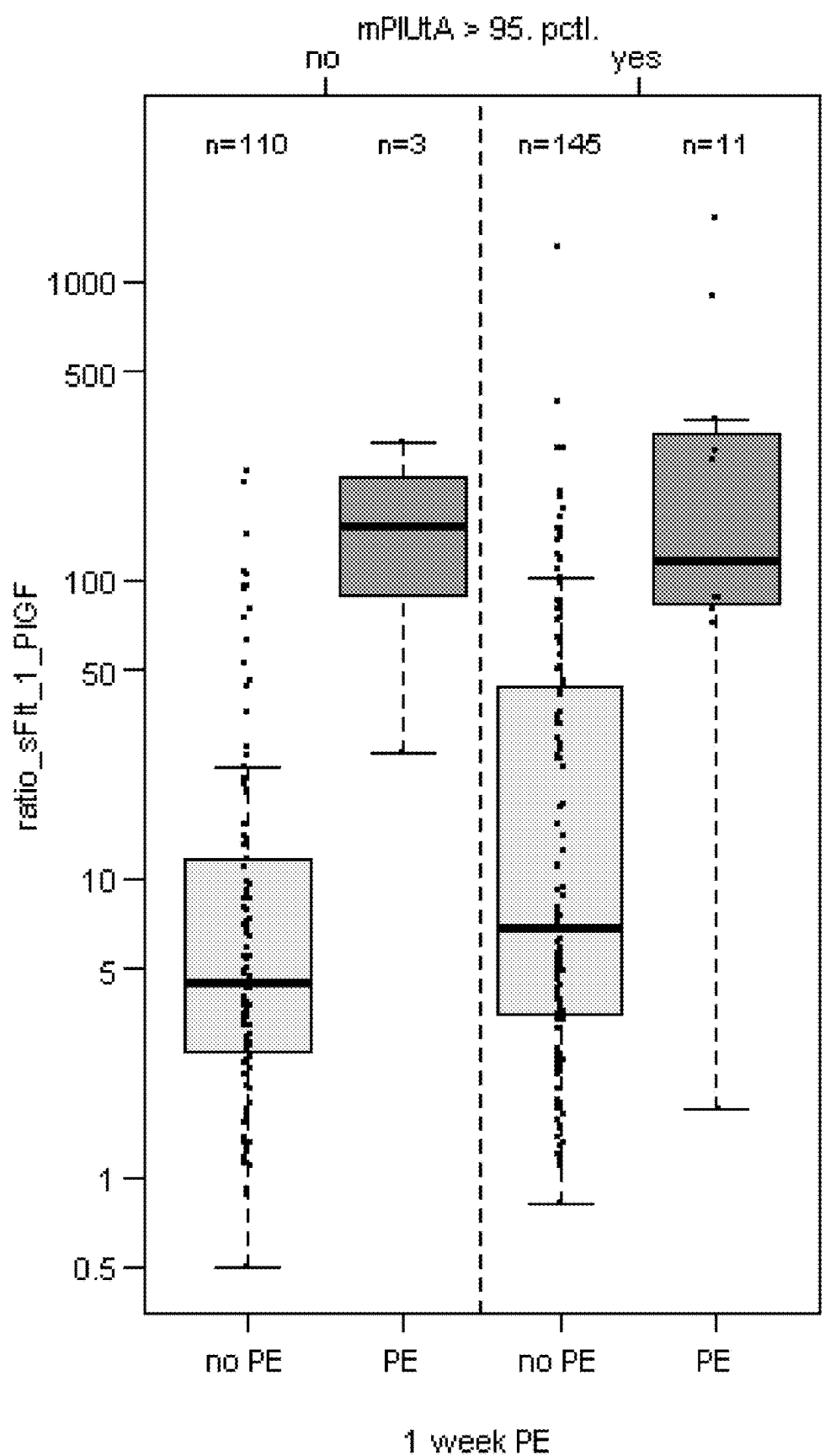
FIG. 7A shows box plot graphs using sFlt-1/PlGF ratio (box plot graphs shown, n=269). The left hand side of the graph shows measurements from patients with abnormal Doppler sonography results (mPI-UtA>95. percentile), the right hand side shows measurements from patients with normal results. Measurements are shown for patients that develop PE/HELLP or not within one week.
Figure 7B:
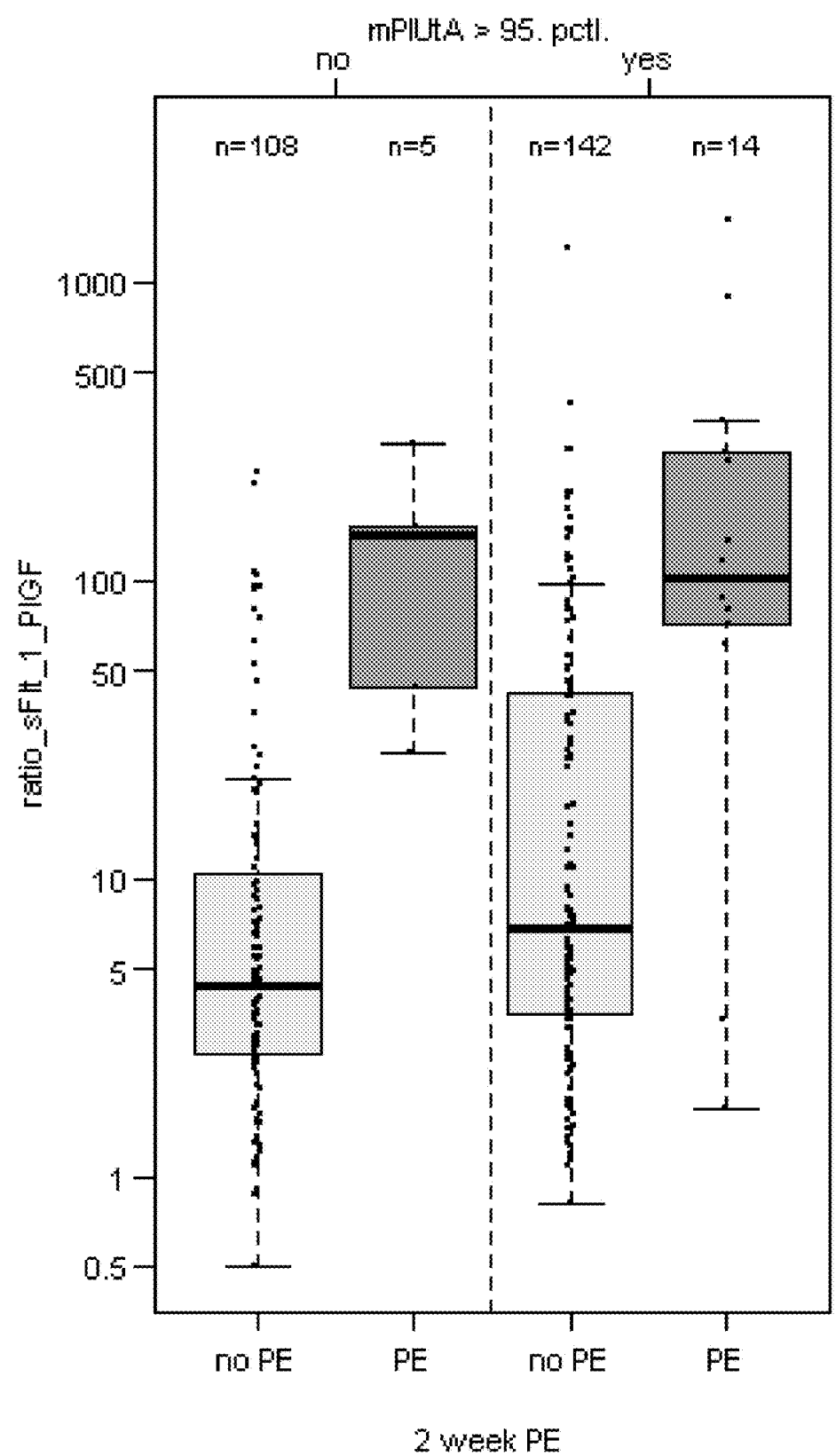
FIG. 7B shows box plot graphs using sFlt-1/PlGF ratio (box plot graphs shown, n=269). The left hand side of the graph shows measurements from patients with abnormal Doppler sonography results (mPI-UtA>95. percentile), the right hand side shows measurements from patients with normal results. Measurements are shown for patients that develop PE/HELLP or not within two weeks.
Figure 7C:
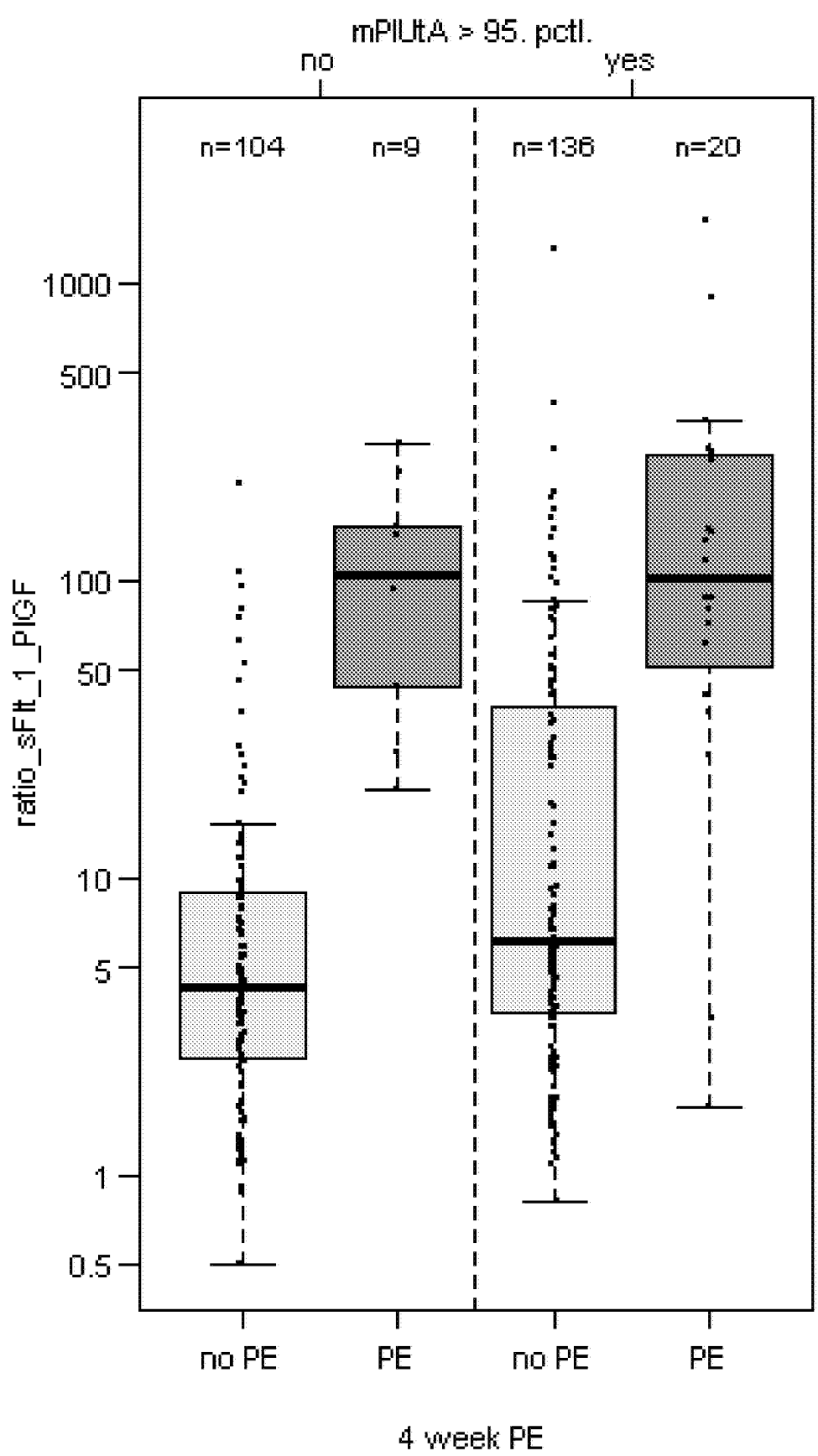
FIG. 7C shows box plot graphs using sFlt-1/PlGF ratio (box plot graphs shown, n=269). The left hand side of the graph shows measurements from patients with abnormal Doppler sonography results (mPI-UtA>95. percentile), the right hand side shows measurements from patients with normal results. Measurements are shown for patients that develop PE/HELLP or not within four weeks. The graphs shown in FIGS. 7A-C show that the sFlt-1/PlGF has potential to predict whether a patient will develop a PE or not both within one week, within two weeks and within four weeks, especially in patients with abnormal Doppler sonography results.

ROC association statistics for the values displayed in FIG. 5A
ROC Association Statistics

| | | | Mann-Whitney | | | |
|---|---|---|---|---|---|---|
| ROC Model | Area | Standard Error | 95% Wald Confidence Limits | | Somers' D (Gini) | Gamma | Tau-a |
| ratio_sFlt_1_PlGF | 0.9262 | 0.0241 | 0.8788 | 0.9735 | 0.8523 | 0.8523 | 0.1139 |
| ratio_endogl_PlGF | 0.9108 | 0.0317 | 0.8487 | 0.9729 | 0.8215 | 0.8215 | 0.1098 |
| tst_res_sFlt_1_pg_ml | 0.9438 | 0.0203 | 0.9041 | 0.9836 | 0.8877 | 0.8877 | 0.1186 |
| tst_res_PlGF_pg_ml | 0.8485 | 0.0410 | 0.7681 | 0.9288 | 0.6969 | 0.6969 | 0.0931 |
| endogl_ng_ml | 0.9238 | 0.0300 | 0.8650 | 0.9827 | 0.8477 | 0.8477 | 0.1133 |

Example 4

Analysis of Preeclampsia as Outcome within 1 Week, Large Cohort (n=269)

In the tables which were used to produce the ROC curve, one can select cut-off values with the target NPV and estimate sensitivity, specificity, and PPV at this cut-off. For all these proportions confidence intervals are available based on the current sample size.

For patients between week 24+/−0 and week 40+/−0 after gestation, a cut off of 38 for the sFlt-1/PlGF ratio determined in a sample obtained at the first visit yielded a NPV of 98.9% (lower limit of two-sided 95% confidence interval (LCL95): 97.3%) to predict preeclampsia, with a sensitivity estimate of 88.2% (LCL95: 72.6%) and a specificity estimate of 79.8% (LCL95: 75.9%). The PPV estimate is 24.4% (LCL95: 17.1%). 123 vs. 372 subjects were test positive/negative at this cut off, 30 out of the 123 test positive are expected to develop PE, and 4 out of the 372 test negative. The results are also summarized in the following table:

TABLE 5

| AUC, LCL95 and UCL95 values, large cohort | | | | |
|---|---|---|---|---|
| Response | Biomarker | AUC | LCL95 | UCL95 |
| PE within 1 week after visit 1 | sFlt_1 | 0.9026 | 0.8417 | 0.9634 |
| PE within 1 week after visit 1 | PlGF | 0.8343 | 0.7697 | 0.8989 |
| PE within 1 week after visit 1 | Endoglin | 0.8702 | 0.811 | 0.9293 |
| PE within 1 week after visit 1 | ratio_sFlt_1_PlGF | 0.897 | 0.8349 | 0.9591 |
| PE within 1 week after visit 1 | ratio_Endogl_PlGF | 0.8693 | 0.8122 | 0.9264 |

TABLE 5-continued

AUC, LCL95 and UCL95 values, large cohort

| Response | Biomarker | AUC | LCL95 | UCL95 |
|---|---|---|---|---|
| PE within 2 weeks after visit 1 | sFlt_1 | 0.8435 | 0.777 | 0.9101 |
| PE within 2 weeks after visit 1 | PlGF | 0.8036 | 0.739 | 0.8682 |
| PE within 2 weeks after visit 1 | Endoglin | 0.849 | 0.7888 | 0.9093 |
| PE within 2 weeks after visit 1 | ratio_sFlt_1_PlGF | 0.848 | 0.7817 | 0.9142 |
| PE within 2 weeks after visit 1 | ratio_Endogl_PlGF | 0.8445 | 0.784 | 0.9049 |
| PE within 4 weeks after visit 1 | sFlt_1 | 0.8513 | 0.7967 | 0.9058 |
| PE within 4 weeks after visit 1 | PlGF | 0.8204 | 0.7699 | 0.8709 |
| PE within 4 weeks after visit 1 | Endoglin | 0.8476 | 0.7986 | 0.8966 |
| PE within 4 weeks after visit 1 | ratio_sFlt_1_PlGF | 0.8598 | 0.8077 | 0.912 |
| PE within 4 weeks after visit 1 | ratio_Endogl_PlGF | 0.8512 | 0.8037 | 0.8987 |

The invention claimed is:

1. A method for identifying and managing a pregnant subject that will not develop preeclampsia for two weeks, comprising:
   a) determining the amounts of the biomarkers soluble FMS-Like Tyrosine Kinase (sFlt-1) and Placental Growth Factor (PlGF) by contacting the biomarkers with an antibody or labeled antibody and detecting the presence of complexes formed between the antibody or labeled antibody and the biomarkers in a sample of said subject, wherein said detecting comprises detecting the complexes by electrochemiluminescence;
   b) calculating a ratio from said amounts of sFlt-1 and PlGF determined in the sample in step (a);
   c) comparing the ratio with a reference value, said reference value is 38+/−20%; and
   d) based on the comparison of step c), identifying a pregnant subject that will not develop preeclampsia for two weeks if the value of the ratio is identical or decreased compared to the reference, and
   e) managing said subject by ambulant monitoring.

2. The method of claim 1, wherein (i) the amount of sFlt-1 is determined in an electrochemiluminescent assay comprising contacting a first aliquot of the sample with a ruthenium-labeled antibody specifically binding a sFlt-1 and determining the amount of complexes formed between said ruthenium-labeled antibody and sFlt-1; and (ii) the amount of PlGF is determined in an electrochemiluminescent assay comprising contacting a second aliquot of the sample with a ruthenium-labeled antibody specifically binding a PlGF and determining the amount of complexes formed between said ruthenium-labeled antibody and PlGF.

3. The method of claim 1, wherein said reference value is 38+/−10%.

* * * * *